United States Patent
Viswanathan et al.

(10) Patent No.: US 10,617,867 B2
(45) Date of Patent: Apr. 14, 2020

(54) SYSTEMS, DEVICES, AND METHODS FOR DELIVERY OF PULSED ELECTRIC FIELD ABLATIVE ENERGY TO ESOPHAGEAL TISSUE

(71) Applicant: Farapulse, Inc., Menlo Park, CA (US)

(72) Inventors: Raju Viswanathan, Mountain View, CA (US); Gary Long, Cincinnati, OH (US); Jean-Luc Pageard, Montreal (CA)

(73) Assignee: Farapulse, Inc., Menlo Park, CA (US)

( * ) Notice: Subject to any disclaimer, the term of this patent is extended or adjusted under 35 U.S.C. 154(b) by 223 days.

(21) Appl. No.: 15/965,564

(22) Filed: Apr. 27, 2018

(65) Prior Publication Data
US 2018/0311497 A1    Nov. 1, 2018

Related U.S. Application Data

(60) Provisional application No. 62/492,032, filed on Apr. 28, 2017.

(51) Int. Cl.
*A61N 1/32* (2006.01)
*A61B 18/12* (2006.01)
(Continued)

(52) U.S. Cl.
CPC .......... *A61N 1/327* (2013.01); *A61B 18/1206* (2013.01); *A61B 18/1492* (2013.01);
(Continued)

(58) Field of Classification Search
None
See application file for complete search history.

(56) References Cited

U.S. PATENT DOCUMENTS

| 4,200,104 A | 4/1980 | Harris |
| 4,470,407 A | 9/1984 | Hussein |

(Continued)

FOREIGN PATENT DOCUMENTS

| EP | 1042990 A1 | 10/2000 |
| EP | 1125549 | 8/2001 |

(Continued)

OTHER PUBLICATIONS

Partial Supplementary European Search Report for European Application No. 13827672.0, dated Mar. 23, 2016, 6 pages.

(Continued)

*Primary Examiner* — Kennedy Schaetzle
(74) *Attorney, Agent, or Firm* — Cooley LLP

(57) ABSTRACT

Systems, devices, and methods for electroporation ablation therapy are disclosed in the context of esophageal ablation. An ablation device may include a first catheter defining a longitudinal axis and a lumen therethrough. A balloon may be coupled to the first catheter. The balloon may be configured to transition between a deflated configuration and an inflated configuration. A second catheter may extend from a distal end of the first catheter lumen. A set of splines including electrodes formed on a surface of each of the splines may couple to the distal end of the first catheter lumen and a distal portion of the second catheter. The second catheter may be configured for translation along the longitudinal axis to transition the set of splines between a first configuration and a second configuration.

18 Claims, 14 Drawing Sheets

(51) Int. Cl.
*A61B 18/14* (2006.01)
*A61N 1/372* (2006.01)
*A61B 18/00* (2006.01)
*A61B 17/00* (2006.01)

(52) U.S. Cl.
CPC ..... *A61N 1/37247* (2013.01); *A61N 1/37258* (2013.01); *A61B 2017/00154* (2013.01); *A61B 2018/00267* (2013.01); *A61B 2018/00285* (2013.01); *A61B 2018/00488* (2013.01); *A61B 2018/00577* (2013.01); *A61B 2018/00613* (2013.01); *A61B 2018/1472* (2013.01); *A61B 2218/002* (2013.01); *A61B 2218/007* (2013.01)

(56) References Cited

U.S. PATENT DOCUMENTS

| | | |
|---|---|---|
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,345,936 A * | 9/1994 | Pomeranz ............ A61B 5/0422 600/374 |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 5,938,660 A * | 8/1999 | Swartz ............... A61B 18/1492 606/45 |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,142,993 A * | 11/2000 | Whayne ............ A61B 18/1492 600/374 |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |

(56) References Cited

U.S. PATENT DOCUMENTS

| | | |
|---|---|---|
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harley et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |

(56) References Cited

U.S. PATENT DOCUMENTS

| | | |
|---|---|---|
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0055674 A1* | 5/2002 | Ben-Haim ............ A61B 5/0215 600/374 |
| 2002/0072738 A1* | 6/2002 | Edwards ............ A61B 18/1485 606/41 |
| 2002/0077627 A1 | 6/2002 | Johnson et al. |
| 2002/0087169 A1 | 7/2002 | Brock et al. |
| 2002/0095176 A1 | 7/2002 | Liddicoat et al. |
| 2002/0111618 A1 | 8/2002 | Stewart et al. |
| 2002/0139379 A1* | 10/2002 | Edwards ............ A61B 18/1485 128/898 |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0083194 A1* | 4/2007 | Kunis ............ A61B 18/1815 606/41 |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0125772 A1* | 5/2008 | Stone ............ A61B 18/1492 606/41 |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |

(56) References Cited

U.S. PATENT DOCUMENTS

| | | |
|---|---|---|
| 2012/0143298 A1* | 6/2012 | Just .................... A61B 5/0422 607/122 |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1* | 2/2014 | Deem .................... A61N 1/05 606/33 |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |

(56) References Cited

U.S. PATENT DOCUMENTS

| | | | |
|---|---|---|---|
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0200497 A1 | 7/2018 | Mickelsen |
| 2018/0303488 A1 | 10/2018 | Hill |
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0231421 A1 | 8/2019 | Viswanathan et al. |
| 2019/0269912 A1 | 9/2019 | Viswanathan et al. |

FOREIGN PATENT DOCUMENTS

| | | | |
|---|---|---|---|
| EP | 0797956 | | 6/2003 |
| EP | 1127552 | | 6/2006 |
| EP | 1340469 | | 3/2007 |
| EP | 1009303 | | 6/2009 |
| EP | 2213729 | | 8/2010 |
| EP | 2425871 | | 3/2012 |
| EP | 1803411 | | 8/2012 |
| EP | 2532320 | A2 | 12/2012 |
| EP | 2587275 | | 5/2013 |
| EP | 2663227 | | 11/2013 |
| EP | 1909678 | | 1/2014 |
| EP | 2217165 | | 3/2014 |
| EP | 2376193 | | 3/2014 |
| EP | 2708181 | | 3/2014 |
| EP | 2777579 | A1 | 9/2014 |
| EP | 2934307 | | 10/2015 |
| EP | 2777585 | | 6/2016 |
| EP | 2382935 | B1 | 3/2018 |
| EP | 3111871 | B1 | 3/2018 |
| EP | 3151773 | B1 | 4/2018 |
| JP | H06-507797 | | 9/1994 |
| JP | 2000-508196 | | 7/2000 |
| JP | 2005-516666 | | 6/2005 |
| JP | 2006-506184 | | 2/2006 |
| JP | 2008-538997 | | 11/2008 |
| JP | 2009-500129 | | 1/2009 |
| JP | 2011-509158 | | 3/2011 |
| JP | 2012-050538 | | 3/2012 |
| WO | WO 92/07622 | | 5/1992 |
| WO | WO 92/21278 | | 12/1992 |
| WO | WO 92/21285 | | 12/1992 |
| WO | WO 94/07413 | | 4/1994 |
| WO | WO 97/24073 | | 7/1997 |
| WO | WO 97/25917 | | 7/1997 |
| WO | WO 97/37719 | | 10/1997 |
| WO | WO 1999/004851 | | 2/1999 |
| WO | WO 1999/022659 | | 5/1999 |
| WO | WO 1999/056650 | | 11/1999 |
| WO | WO 1999/059486 | | 11/1999 |
| WO | WO 2002/056782 | | 7/2002 |
| WO | WO 2003/053289 | | 7/2003 |
| WO | WO 2003/065916 | | 8/2003 |
| WO | WO 2004/045442 | | 6/2004 |
| WO | WO 2004/086994 | | 10/2004 |
| WO | WO 2006/115902 | | 11/2006 |
| WO | WO 2007/006055 | | 1/2007 |
| WO | WO 2007/079438 | | 7/2007 |
| WO | WO 2009/082710 | | 7/2009 |
| WO | WO 2009/089343 | | 7/2009 |
| WO | WO 2009/137800 | | 11/2009 |
| WO | WO 2010/014480 | | 2/2010 |
| WO | WO 2011/028310 | | 3/2011 |
| WO | WO 2011/154805 | | 12/2011 |
| WO | WO 2012/051433 | | 4/2012 |
| WO | WO 2012/153928 | | 11/2012 |
| WO | WO 2013/019385 | | 2/2013 |
| WO | WO 2014/025394 | | 2/2014 |
| WO | WO 2014/031800 | | 2/2014 |
| WO | WO 2014/160832 | | 10/2014 |
| WO | WO 2015/066322 | | 5/2015 |
| WO | WO 2015/099786 | | 7/2015 |
| WO | WO 2015/103530 | | 7/2015 |
| WO | WO 2015/103574 | | 7/2015 |
| WO | WO 2015/130824 | | 9/2015 |
| WO | WO 2015/143327 | | 9/2015 |
| WO | WO 2015/171921 | | 11/2015 |
| WO | WO 2015/175944 | | 11/2015 |
| WO | WO 2015/192018 | | 12/2015 |
| WO | WO 2015/192027 | | 12/2015 |
| WO | WO 2016/059027 | | 4/2016 |
| WO | WO 2016/060983 | | 4/2016 |
| WO | WO 2016/081650 | | 5/2016 |
| WO | WO 2016/090175 | | 6/2016 |
| WO | WO 2017/119934 | | 7/2017 |
| WO | WO 2017/120169 | | 7/2017 |
| WO | WO 2017/192477 | | 11/2017 |
| WO | WO 2017/192495 | | 11/2017 |
| WO | WO 2017/218734 | | 12/2017 |
| WO | WO 2018/200800 | | 11/2018 |

OTHER PUBLICATIONS

Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 15 pages.
Office Action for U.S. Appl. No. 15/201,997, dated Dec. 17, 2018, 17 pages.
International Search Report and Written Opinion for International Application No. PCT/US2018/050660, dated Nov. 26, 2018, 13 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.

(56) References Cited

OTHER PUBLICATIONS

Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Office Action for U.S. Appl. No. 15/795,062, dated Dec. 19, 2017, 14 pages.
Office Action for U.S. Appl. No. 15/795,062, dated Apr. 9, 2018, 20 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
Du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
Van Driel, V.J.H.M. et al., "Pulmonary Vein Stenosis After Catheter Ablation Electroporation Versus Radiofrequency," Circ Arrhythm Electrophysiol., 7(4):734-738 (2014).
Van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for Japanese Application No. 2018-036714, dated Jan. 16, 2019, 8 pages.
Office Action for U.S. Appl. No. 15/201,983, dated Apr. 3, 2019, 16 pages.
Office Action for U.S. Appl. No. 15/341,523, dated Jan. 29, 2019, 10 pages.
Office Action for U.S. Appl. No. 15/795,075, dated Apr. 10, 2019, 11 pages.
Office Action for U.S. Appl. No. 15/672,916, dated Apr. 9, 2019, 31 pages.
Partial European Search Report for European Application No. 18170210.1, dated Feb. 14, 2019, 13 pages.
Office Action for U.S. Appl. No. 15/970,404, dated Apr. 12, 2019, 20 pages.
Office Action for U.S. Appl. No. 15/917,194, dated Apr. 29, 2019, 10 pages.
Office Action for U.S. Appl. No. 15/795,062, dated May 3, 2019, 21 pages.
International Search Report and Written Opinion for International Application No. PCT/US2019/014226, dated Apr. 29, 2019, 15 pages.
Extended European Search Report for European Application No. 18189811.5, dated May 14, 2019, 7 pages.
International Search Report and Written Opinion for International Application No. PCT/US2019/017322, dated May 10, 2019, 15 pages.
Office Action for U.S. Appl. No. 15/341,512, dated Aug. 1, 2019, 19 pages.
Office Action for U.S. Appl. No. 15/341,523, dated Jul. 30, 2019, 8 pages.

(56) References Cited

OTHER PUBLICATIONS

Office Action for U.S. Appl. No. 15/795,075, dated Jul. 31, 2019, 12 pages.
Office Action for U.S. Appl. No. 15/484,969, dated Sep. 4, 2019, 12 pages.
Office Action for U.S. Appl. No. 15/354,475, dated May 23, 2019, 7 pages.
Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
Office Action for U.S. Appl. No. 16/181,027, dated Sep. 4, 2019, 12 pages.
Office Action for U.S. Appl. No. 16/240,066, dated May 29, 2019, 7 pages.
Extended European Search Report for European Application No. 18170210.1, dated May 17, 2019, 11 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
International Search Report and Written Opinion for International Application No. PCT/US2019/028943, dated Sep. 17, 2019, 17 pages.

\* cited by examiner

SYSTEMS, DEVICES, AND METHODS FOR DELIVERY OF PULSED ELECTRIC FIELD ABLATIVE ENERGY TO ESOPHAGEAL TISSUE

CROSS-REFERENCE TO RELATED APPLICATIONS

This application claims priority to U.S. Provisional Application No. 62/492,032, filed on Apr. 28, 2017, and titled "SYSTEMS, DEVICES, AND METHODS FOR DELIVERY OF PULSED ELECTRIC FIELD ABLATIVE ENERGY TO ESOPHAGEAL TISSUE", the disclosure of which is hereby incorporated by reference in its entirety.

BACKGROUND

The generation of pulsed electric fields for tissue therapeutics has moved from the laboratory to clinical applications over the past two decades, while the effects of brief pulses of high voltages and large electric fields on tissue have been investigated for the past forty years or more. Application of brief high DC voltages to tissue may generate locally high electric fields typically in the range of hundreds of volts per centimeter that disrupt cell membranes by generating pores in the cell membrane. While the precise mechanism of this electrically-driven pore generation or electroporation continues to be studied, it is thought that the application of relatively brief and large electric fields generates instabilities in the lipid bilayers in cell membranes, causing the occurrence of a distribution of local gaps or pores in the cell membrane. This electroporation may be irreversible if the applied electric field at the membrane is larger than a threshold value such that the pores do not close and remain open, thereby permitting exchange of biomolecular material across the membrane leading to necrosis and/or apoptosis (cell death) without damage to the tissue scaffolding and structural matrix. Subsequently, the surrounding tissue may heal naturally.

In the context of gastric reflux and esophageal disease, the condition of Barrett's esophagus can generate inflammation of the esophageal mucosal lining that, in many cases, may represent a pre-cancerous stage that could develop later into a tumor. Early intervention and treatment of this condition is often warranted. Current techniques to treat this condition involve the use of an RF (Radio Frequency) balloon or cryo-balloon for ablation of the mucosal lining.

These existing techniques involving thermal ablation (heating or cooling) can cause discomfort and the therapy delivery process can take tens of minutes, while at the same time the treatment is not always effective as there may remain localized regions of tissue that have not been treated. There is a need for alternative treatment approaches that are rapid, cause minimal discomfort and are highly effective.

Given that appropriate pulsed DC voltages may drive irreversible electroporation in tissue under the right circumstances, there is an opportunity to address the unmet need for flexible, atraumatic devices that effectively deliver high pulsed DC voltage electroporation ablation therapy selectively to esophageal tissue in the esophagus while minimizing damage to healthy tissue. This need is addressed in the present disclosure.

SUMMARY

Described here are systems, devices, and methods for ablating tissue through irreversible electroporation, in particular ablating esophageal tissue for the treatment of the condition of Barrett's esophagus. Generally, an apparatus may include a first catheter defining a longitudinal axis and a lumen therethrough. A balloon may be coupled to the first catheter, the balloon may be configured to transition between a deflated configuration and an inflated configuration. A second catheter may extend from a distal end of the first catheter lumen, the second catheter including a distal cap. A set of splines may have a proximal portion coupled to a distal end of the first catheter lumen and a distal portion coupled to the distal cap. Each spline may include an intermediate portion between the proximal portion and the distal portion. The intermediate portion may include a set of electrodes formed on a surface of each of the splines. Each electrode may have an insulated electrical lead associated herewith. The insulated electrical leads may be disposed in a body of each of the set of splines. The second catheter may be configured for translation along the longitudinal axis to transition the set of splines between a first configuration and a second configuration. In the second configuration, each intermediate portion of the set of splines may be biased farther away from the longitudinal axis relative to the respective intermediate portion in the first configuration.

In some embodiments, an apparatus may include a first catheter defining a longitudinal axis and a lumen therethrough. A balloon may be coupled to a distal end of the first catheter. The balloon may be configured to transition between a deflated configuration and an inflated configuration. A second catheter may extend from a distal end of the first catheter lumen. The second catheter may include a distal cap. A set of splines may have a proximal portion coupled to a distal end of the first catheter lumen and a distal portion coupled to the distal cap. Each spline may include an intermediate portion between the proximal portion and the distal portion. The intermediate portion may include a set of electrodes formed on a surface of each of the splines, each electrode having an insulated electrical lead associated herewith. The insulated electrical leads may be disposed in a body of each of the set of splines. The second catheter may be configured to transition the splines between a first configuration and a second configuration. In the second configuration, each spline of the set of splines may be biased farther away from the longitudinal axis relative to the respective spline in the first configuration.

In some embodiments, a system may include a signal generator configured for generating a pulse waveform. An ablation device may be coupled to the signal generator and configured for receiving the pulse waveform. The ablation device may include a handle, a first catheter defining a longitudinal axis and a lumen therethrough, and a balloon coupled to the first catheter. The balloon may be configured to transition between a deflated configuration and an inflated configuration. A second catheter may extend from a distal end of the first catheter lumen, the second catheter including a distal cap. A set of splines may have a proximal portion coupled to a distal end of the first catheter lumen and a distal portion coupled to the distal cap. Each spline may include an intermediate portion between the proximal portion and the distal portion. The intermediate portion may include a set of electrodes formed on a surface of each of the splines, each electrode having an insulated electrical lead associated herewith. The insulated electrical leads may be disposed in a body of each of the set of splines. The second catheter may be configured for translation along the longitudinal axis to transition the set of splines between a first configuration and a second configuration. In the second configuration, each intermediate portion of the set of splines may be biased away from the longitudinal axis relative to the respective intermediate portion in the first configuration.

In some embodiments, the set of splines may bow radially outward from the longitudinal axis in the second configuration. In some embodiments, the set of splines may bias away from the longitudinal axis in the second configuration. In some embodiments, an actuator may be coupled to the set of splines and the distal cap. The actuator may be configured to transition the set of splines between the first configuration and the second configuration and the balloon between a deflated configuration and an inflated configuration. In some embodiments, the second catheter may have a set of fluid openings. In some embodiments, the set of openings may be oriented towards at least one spline of the set of splines. In some embodiments, the balloon is a first balloon and the apparatus includes a second balloon. The second balloon may be coupled to the second catheter. The second balloon may be configured to transition between a deflated configuration and an inflated configuration. In some embodiments, the set of electrodes on adjacent splines may have opposite polarities. In some embodiments, the set of splines when deployed in the second configuration may form a shape with an effective cross-sectional diameter at its largest portion of between about 10 mm and about 35 mm. In some embodiments, the set of splines may include between 3 splines and 14 splines. In some embodiments, each spline of the set of splines may have a diameter of between about 1 mm and about 4 mm. In some embodiments, each electrode of the set of electrodes may have a diameter of between about 1 mm and about 4 mm. In some embodiments, the insulated electrical leads may be disposed in a body of the second catheter, the insulated electrical leads configured for sustaining a voltage potential of at least about 300 V without dielectric breakdown of its corresponding insulation. In some embodiments, the balloon may be coupled to a distal end of the first catheter. In some embodiments, the second balloon may be coupled to a distal end of the second catheter.

In some embodiments, the pulse waveform may include a first level of a hierarchy of the pulse waveform includes a first set of pulses, each pulse having a pulse time duration, a first time interval separating successive pulses. A second level of the hierarchy of the pulse waveform may include a plurality of first sets of pulses as a second set of pulses, a second time interval separating successive first sets of pulses, the second time interval being at least three times the duration of the first time interval. A third level of the hierarchy of the pulse waveform may include a plurality of second sets of pulses as a third set of pulses, a third time interval separating successive second sets of pulses, the third time interval being at least thirty times the duration of the second level time interval.

In some embodiments, an apparatus may include a coil having a set of loops, each loop of the set of loops including a set of independently addressable electrodes formed on a surface of each of the loops. Each electrode may have an insulated electrical lead associated herewith, the insulated electrical leads disposed in a body of each of the loops. A balloon may be coupled to the coil. The balloon may be configured to transition between a deflated configuration and an inflated configuration.

In some embodiments, a winding pitch of the set of loops may be substantially equal. In some embodiments, a length of the set of loops may be between about 35 mm and about 50 mm. In some embodiments, a winding pitch of the set of loops may be between about 2 mm and about 16 mm. In some embodiments, a winding pitch may differ between at least two loops of the set of loops. In some embodiments, a winding pitch of a proximal loop of the set of loops may be between about 2 mm and about 7 mm, and the winding pitch of a distal loop of the set of loops is between about 6 mm and about 16 mm. In some embodiments, the set of electrodes may form a shape with an effective cross-sectional diameter at its largest portion of between about 10 mm and about 35 mm. In some embodiments, the insulated electrical leads may be configured for sustaining a voltage potential of at least about 700 V without dielectric breakdown of its corresponding insulation. In some embodiments, the set of electrodes on adjacent loops may have opposite polarities. In some embodiments, the balloon is a first balloon and the apparatus includes a second balloon. The second balloon may be coupled to a distal end of the coil. The second balloon may be configured to transition between the deflated configuration and the inflated configuration. In some embodiments, the second balloon may be coupled proximal to the set of loops.

In some embodiments, an apparatus may include a first catheter defining a longitudinal axis and a lumen therethrough. A balloon may be coupled to the first catheter. The balloon may be configured to transition between a deflated configuration and an inflated configuration. A set of electrodes may be coupled to a distal end of the first catheter. The set of electrodes may be arranged substantially perpendicular to the longitudinal axis, each electrode having an insulated electrical lead associated herewith, the insulated electrical leads disposed in the catheter lumen.

In some embodiments, the set of electrodes may form a shape with an effective cross-sectional diameter at its largest portion of between about 10 mm and about 35 mm. In some embodiments, the insulated electrical leads may be disposed in a body of the first catheter, the insulated electrical leads configured for sustaining a voltage potential of at least about 700 V without dielectric breakdown of its corresponding insulation. In some embodiments, a second catheter may be slidably disposed within the lumen of the first catheter. A second electrode may be coupled to a distal end of the second catheter. In some embodiments, the balloon is a first balloon and the apparatus includes a second balloon. The second balloon may be coupled to the first catheter. The second balloon may be configured to transition between the deflated configuration and the inflated configuration. In some embodiments, the second balloon may be coupled to a distal end of the apparatus.

In some embodiments, a method of treating Barret's esophagus via irreversible electroporation may include generating a pulse waveform and delivering the pulse waveform to a portion of an esophagus of a patient via one or more splines of a set of splines of an ablation device. The ablation device may include a first catheter defining a longitudinal axis and a lumen therethrough; a balloon coupled to the first catheter; a second catheter extending from a distal end of the first catheter lumen, the second catheter including a distal cap, wherein the set of splines have a proximal portion coupled to a distal end of the first catheter lumen and a distal portion coupled to the distal cap, each spline including an intermediate portion between the proximal portion and the distal portion, the intermediate portion including a set of electrodes formed on a surface of each of the splines, each electrode having an insulated electrical lead associated herewith, the insulated electrical leads disposed in a body of each of the set of splines.

In some embodiments, the ablation device may be advanced into an inferior portion of the esophagus. The ablation device may transition from a first configuration to a second configuration. The first configuration may include the set of splines arranged substantially parallel to a longitudinal axis of the ablation device and the second configuration may include the set of splines substantially biased away from the longitudinal axis. In some embodiments, each insulated electrical lead may be configured for sustaining a voltage potential of at least about 700 V without dielectric breakdown of its corresponding insulation.

In some embodiments, the set of splines may include a group of electrodes, the group of electrodes including the set of electrodes of each spline of the set of splines. A first electrode of the group of electrodes may be configured as an anode. A second electrode of the group of electrodes may be configured as a cathode. The pulse waveform may be delivered to the first electrode and the second electrode.

In some embodiments, a first set of electrodes of a first spline of the set of splines may be configured as anodes. A second set of electrodes of a second spline of the set of splines may be configured as cathodes. The pulse waveform may be delivered to the first set of electrodes and the second set of electrodes. In some of these embodiments, the set of splines may be advanced and disposed within a lumen of a first catheter, away from a distal end of the first catheter. In some embodiments, the ablation device may be disposed in an inferior portion of the esophagus, and in contact with or proximity to esophageal tissue. In some embodiments, the balloon is a first balloon, and the ablation device includes a second balloon. The first balloon and the second balloon may transition from a deflated configuration to an inflated configuration. In some embodiments, the ablation device may transition from the inflated configuration to the deflated configuration. In some embodiments, the ablation device may include a catheter defining a set of openings, the catheter coupled to the set of splines. A fluid may be infused through the set of openings. In some embodiments, the fluid may be held between the first balloon and the second balloon to increase a conductivity of a space between the first balloon and the second balloon, and pulsed electric field ablation delivered to esophageal tissue with the fluid filling the space around the electrodes. In some embodiments, fluid may be suctioned into the set of openings after ablation delivery is completed. In some embodiments, pulsed electric field ablation energy may be delivered through the electrodes of the ablation device.

DETAILED DESCRIPTION

Figure 1:
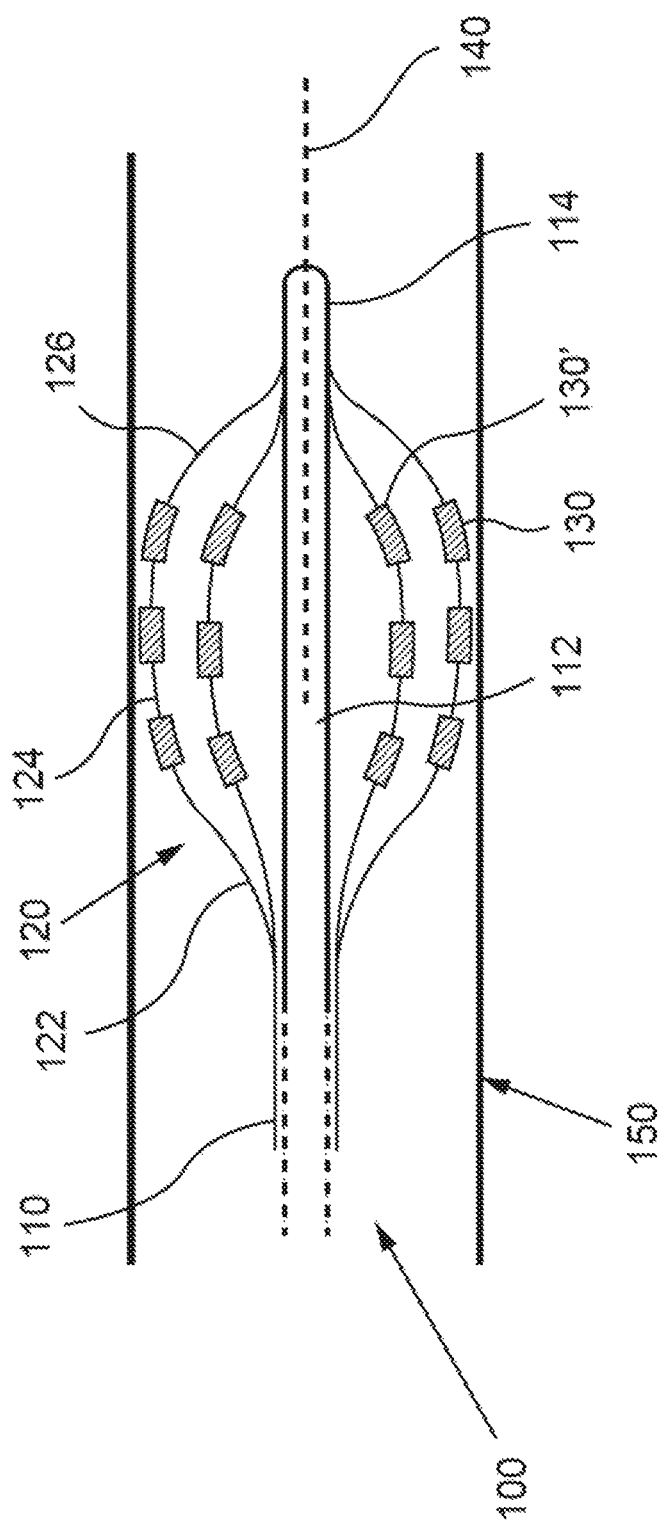
FIG. 1 is a side view of an ablation device disposed in an esophagus, according to other embodiments.

Described herein are systems, devices, and methods for selective and rapid application of pulsed electric fields to ablate tissue by irreversible electroporation. Generally, the systems, devices, and methods described herein may be used to generate large electric field magnitudes at desired regions of interest and reduce peak electric field values elsewhere in order to reduce unnecessary tissue damage and electrical arcing. An ablation device may include a set of configurable electrodes for delivery of ablation energy. In some embodiments, the ablation device and/or a portion thereof may be configured to transition between a compact configuration and an expanded configuration.

An irreversible electroporation system as described herein may include a signal generator and a processor configured to apply one or more voltage pulse waveforms to a selected set of electrodes of an ablation device to deliver energy to a region of interest (e.g., ablation energy for a region of tissue in an esophagus) and provide a highly configurable set of electrode channels (e.g., allow independent and arbitrary electrode selection). The pulse waveforms disclosed herein may aid in therapeutic treatment of the condition of Barrett's esophagus. In order to deliver the pulse waveforms generated by the signal generator, one or more electrodes of the ablation device may have an insulated electrical lead configured for sustaining a voltage potential of at least about 700 V without dielectric breakdown of its corresponding insulation. In some embodiments, the electrodes may be independently addressable such that each electrode may be controlled (e.g., deliver energy) independently of any other electrode of the device. In other embodiments, subsets of electrodes may be electrically wired together for efficient delivery of pulsed electric field energy.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may include one or more of the methods, systems, and devices described in International Application Serial No. PCT/US2016/057664, filed on Oct. 19, 2016, and titled "SYSTEMS, APPARATUSES AND METHODS FOR DELIVERY OF ABLATIVE ENERGY TO TISSUE," the contents of which are hereby incorporated by reference in its entirety.

Generally, to ablate tissue, the device may be advanced into the esophagus to a target location. In some embodiments, the ablation device may transform into different configurations (e.g., compact and expanded) to position the device within the esophageal space. The methods described here may include placing tissue (e.g., inner wall of the esophagus) in contact with the electrodes. A pulse waveform may be generated and delivered to one or more electrodes of the device to ablate tissue. In some embodiments, the pulse waveform may be generated in synchronization with a pacing signal of the heart to avoid disruption of the sinus rhythm of the heart. In some embodiments, the electrodes may be configured in anode-cathode (e.g., bipole) subsets. The pulse waveform may include hierarchical waveforms to aid in tissue ablation and reduce damage to healthy tissue.

I. Systems

Overview

Disclosed herein are systems and devices configured for tissue ablation via the selective and rapid application of voltage pulse waveforms to aid tissue ablation, resulting in irreversible electroporation. Generally, a system for ablating tissue described here may include a signal generator and an ablation device having one or more electrodes for the selective and rapid application of DC voltage to drive electroporation. As described in more detail herein, the systems and devices described herein include one or more ablation devices configured to ablate tissue of the esophagus. Voltages may be applied to a selected subset of the electrodes, with independent subset selections for anode and cathode electrode selections. The ablation device may be coupled to one or more electrode channels of the signal generator. Each electrode channel, or subset of electrode channels, may be independently configured as an anode or cathode and a voltage pulse waveform may be delivered through one or more of the electrode channels in a predetermined sequence.

Figure 8:
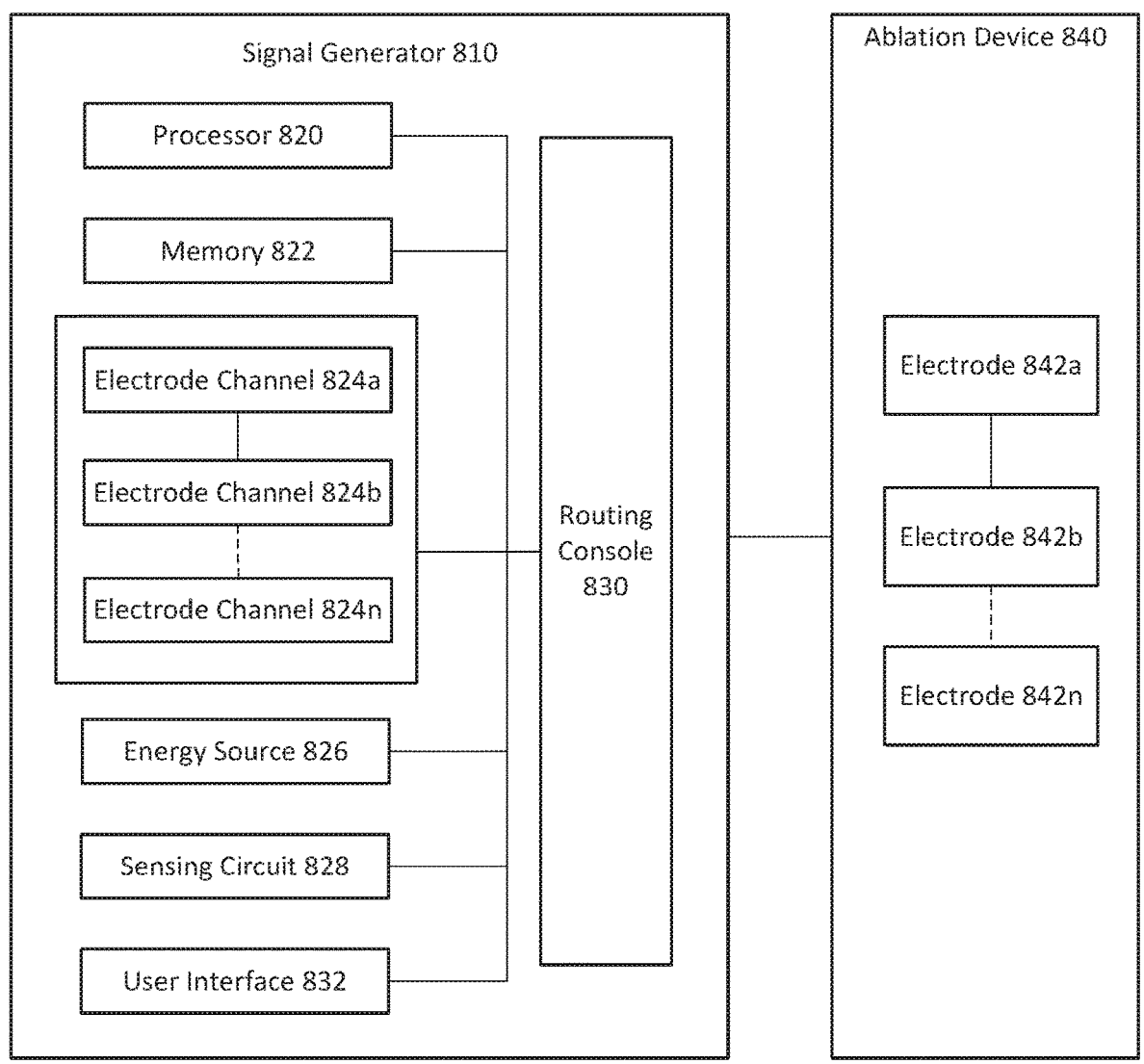
FIG. 8 is a block diagram of an electroporation system, according to embodiments.

FIG. 8 illustrates an ablation system (800) configured to deliver voltage pulse waveforms for tissue ablation. The system (800) may include a signal generator (810) and ablation device (840). The signal generator (810) may be coupled to at least one ablation device (840) having a set of one or more electrodes (842a, 842b, . . . , 842n).

Signal Generator

The signal generator (810) may be configured to generate pulse waveforms for irreversible electroporation of tissue, such as, for example, heart tissue. The signal generator (810) may be a voltage pulse waveform generator and deliver a pulse waveform to a set of electrodes (842a, 842b, . . . , 842n,) of the ablation device (840). The signal generator (810) may generate and deliver several types of signals including, but not limited to, radiofrequency (RF), direct current (DC) impulses (such as high-voltage, ultra-short pulses used in electroporation), stimulus range impulses, and/or hybrid electrical impulses. For example, the signal generator (810) may generate monophasic (DC) pulses and biphasic (DC and AC) pulses. The signal generator (810) may include a processor (820), memory (822), a set of electrode channels (824a, 824b, . . . , 824n), energy source (826), sensing circuit (828), routing console (830), and user interface (832). One or more signal generator components may be coupled using a communication bus. The processor (820) may incorporate data received from one or more of memory (822), electrode channels (824a, 824b, . . . , 824n), energy source (826), sensing circuit (828), routing console (830), user interface (832), ablation device (840) to determine the parameters (e.g., amplitude, width, duty cycle, timing, etc.) of the voltage pulse waveform to be generated by the signal generator (810). The memory (822) may further store instructions to cause the processor (820) to execute modules, processes and/or functions associated with the system (800), such as pulse waveform generation and delivery, and/or electrode channel configuration. For example, the memory (822) may be configured to store anode/cathode configuration data, electrode channel configuration data, pulse waveform data, fault data, energy discharge data, heart pacing data, patient data, clinical data, procedure data, sensor data, temperature data, and/or the like.

In some embodiments, the ablation device (840) may include a catheter configured to receive and/or deliver the pulse waveforms described herein. For example, the ablation device (840) may be introduced into a lumen of an esophagus and positioned to align one or more electrodes (842a, 842b, . . . , 842n) to esophageal tissue (e.g., mucosa, submucosa), and then deliver the pulse waveforms to ablate tissue. The ablation device (840) may include one or more electrodes (842a, 842b, . . . , 842n), which may, in some embodiments, be a set of independently addressable electrodes. For example, the electrodes (842a, 842b, . . . , 842n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrodes (842a, 842b, . . . , 842n) may include any number of electrodes, for example, 2, 3, 4, 5, 6, 7, 8, 9, 10, 12, or more electrodes. In other embodiments, predetermined subsets of electrodes may be electrically wired together so that each such subset is independently addressable. In some embodiments, the methods, systems, and devices disclosed herein may include one or more of the methods, systems, and devices described in U.S. patent application Ser. No. 15/499,804, filed on Apr. 27, 2017, and titled "SYSTEMS, DEVICES, AND METHODS FOR SIGNAL GENERATION," and International Application Serial No. PCT/US17/12099, filed on Jan. 4, 2017, and titled "SYSTEMS, DEVICES, AND METHODS FOR DELIVERY OF PULSED ELECTRIC FIELD ABLATIVE ENERGY TO ENDOCARDIAL TISSUE," and International Application Serial No. PCT/US2013/031252, filed on Mar. 14, 2013, and titled "CATHETERS, CATHETER SYSTEMS, AND METHODS FOR PUNCTURING THROUGH A TISSUE STRUCTURE AND ABLATING A TISSUE REGION," the contents of which are hereby incorporated by reference in its entirety.

In some embodiments, the processor (820) may be any suitable processing device configured to run and/or execute a set of instructions or code and may include one or more data processors, image processors, graphics processing units, physics processing units, digital signal processors, and/or central processing units. The processor (820) may be, for example, a general purpose processor, Field Programmable Gate Array (FPGA), an Application Specific Integrated Circuit (ASIC), and/or the like. The processor (820) may be configured to run and/or execute application processes and/or other modules, processes and/or functions associated with the system and/or a network associated therewith (not shown). In some embodiments, the processor may include both a microcontroller unit and an FPGA unit, with the microcontroller sending electrode sequence instructions to the FPGA. The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

In some embodiments, the memory (822) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (822) may store instructions to cause the processor (820) to execute modules, processes and/or functions associated with the system (800), such as pulse waveform generation and/or electrode channel configuration.

In some embodiments, a set of electrode channels (824a, 824b, . . . , 824n) may include a set of active solid-state switches. The set of electrode channels (824a, 824b, . . . , 824n) may be configured in a number of ways, including independent anode/cathode configuration for each electrode channel. For example, the electrode channels (824a, 824b, . . . , 824n) may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. The set of electrode channels (824a, 824b, . . . , 824n) may include any number of channels, for example, 2, 3, 4, 5, 6, 7, 8, 9, 10, 12, or more electrode channels. Energy delivery may use any combination of electrode channels (824a, 824b, . . . , 824n) and any order for an energy delivery sequence. The energy delivered may be an RF and/or any tissue ablation energy.

The set of electrode channels (824a, 824b, . . . , 824n) may be coupled to a routing console (830) to deliver energy to a set of electrodes (842) coupled to the routing console (830). The set of electrode channels (824a, 824b, . . . , 824n) may be coupled to an energy source (826) to receive energy (e.g., a pulse waveform). Processor (820) may be coupled to each electrode channel (824a, 824b, . . . , 824n) to configure an anode/cathode configuration for each electrode channel (824), which may be configured on a per pulse basis, per operator input, and/or the like. The processor (820) and energy source (826) may be collectively configured to deliver a pulse waveform to the set of electrodes (842) through the set of electrode channels (824a, 824b, . . . , 824n). In some embodiments, each electrode channel (824a, 824b, . . . , 824n) may include an electronic switch (e.g., bipolar transistor) and a drive circuit, as described in detail herein. In some embodiments, each electrode channel (824a, 824b, . . . , 824n) may have a bootstrap configuration for low and high frequency operation. For example, the pulse duration of voltage pulses delivered through an electrode channel may be in the range of between about 1 microsecond and about 1000 microseconds. In biphasic mode, this corresponds to an approximate frequency range of between about 500 Hz and about 500 KHz for the frequency associated with the voltage pulses.

In some embodiments, a controller including the processor (820) and memory (822) may be coupled to each electrode of the set of electrodes (842). The controller may be configured to generate a pulse waveform and configure the set of electrodes (842) for pulse waveform delivery. The pulse waveform may be delivered to the set of electrodes (842).

In some embodiments, an energy source (826) may be configured to convert and supply energy to a set of electrodes (842) coupled to the signal generator (810). The energy source (826) of the signal generator (810) may include a DC power supply and be configured as an AC/DC switcher. In some embodiments, an energy source (826) of the signal generator (810) may deliver rectangular-wave pulses with a peak maximum voltage of up to about 7 kV into a device with an impedance in the range of about 30Ω to about 3000Ω for a maximum duration of about 100 μs. In some of these embodiments, the energy source (826) may be configured to store energy. For example, the energy source (826) may include one or more capacitors to store energy from a power supply. While these examples are included for purely non-limiting illustrative purposes, it is noted that a variety of pulse waveforms with a range of pulse durations, intervals between pulses, pulse groupings, etc. may be generated depending on the clinical application.

In some embodiments, a sensing circuit (828) may be configured to determine an amount of current being delivered to a device coupled to the signal generator (810) (e.g., electrode (842) coupled to the electrode channel (824)). As described in more detail herein, the sensing circuit (828) may also be used to classify an electrode channel fault, monitor capacitor discharge, and/or sense arcing. In some embodiments, the sensing circuit (828) may be a direct current sensing circuit and/or a low-side sensing circuit. The sensing circuit may include one or more operational amplifiers, difference amplifiers (DA), instrumentation amplifiers (IA), and/or current shunt monitors (CSM).

In some embodiments, the routing console (830) may be configured to electrically couple a set of electrodes (842) of an ablation device (840) to a set of electrode channels (824a, 824b, . . . , 824n). The routing console (830) may be configured to selectively deliver energy to the set of electrodes (842) using the set of electrode channels (824a, 824b, . . . , 824n). One or more ablation devices (840) each having a set of electrodes (842) may be coupled to the routing console (830). The set of electrodes (842) may include any number of electrodes, for example, 1, 2, 3, 4, 5, 6, 7, 8, 9, 10, 12, or more electrodes.

In some embodiments, the electrode channels (824a, 824b, . . . , 824n) configured for energy delivery (e.g., configured as an anode/cathode pair of electrode channels)

may not be adjacent to each other. For example, the set of electrode channels (824a, 824b, . . . , 824n) may include a set of N electrode channels (824a, 824b, . . . , 824n) in a parallel array. In one embodiment, a first electrode channel may correspond to a first electrode channel (824a) in the parallel array of N electrode channels (824a, 824b, . . . , 824n). One or more of a second and third electrode channel (824b, 824c) may not be adjacent to the first electrode channel (824a) in the parallel array of N electrode channels (824a, 824b, . . . , 824n).

A multi-electrode ablation device may allow targeted and precise energy delivery to tissue. In some embodiments, the electrodes (842) of an ablation device (840) may be configured for energy delivery (e.g., as an anode/cathode pair of electrodes (842) and may be disposed on adjacent or opposing splines of the ablation device (840). For example, an ablation device may include a first spline having a set of first electrodes as a parallel array of M electrodes and a second spline having a set of second electrodes as a parallel array of M electrodes. The signal generator (810) coupled to the ablation device (840) may include a set of electrode channels (824a, 824b, . . . , 824n) having N electrode channels corresponding to the M electrodes (842n) of the ablation device (840). In one embodiment, the first electrode channel (824a) of the N electrode channels (824a, 824b, . . . , 824n) may correspond to a first electrode in the parallel array of M electrodes of the first spline. One or more of second and third electrode channel (824b, 824c) of the N electrode channels (824n) may not correspond to any of the electrodes adjacent to the first electrode in the parallel array of M electrodes. For example, the second electrode channel (842b) may correspond to a second electrode in the parallel array of M electrodes of the second spline.

Configurable electrode channel and electrode selection may provide flexibility in positioning the electrodes for ablating a desired region of interest, as described in more detail herein. The routing console (830) may receive input from the processor (820) and/or user interface (832) for electrode channel selection and energy delivery to one or more electrodes (842).

In some embodiments, a user interface (832) may be configured as a communication interface between an operator and the system (800). The user interface (832) may include an input device and output device (e.g., touch surface and display). For example, patient data from memory (822) may be received by user interface (832) and output visually and/or audibly. Electric current data from sensing circuit (828) may be received and output on a display of user interface (832). As another example, operator control of an input device having one or more buttons, knobs, dials, switches, trackball, touch surface, and/or the like, may generate a control signal to the signal generator (810) and/or ablation device (840).

In some embodiments, an input device of the user interface (832) may include a touch surface for operator input and may be configured to detect contact and movement on the touch surface using any of a plurality of touch sensitivity technologies including capacitive, resistive, infrared, optical imaging, dispersive signal, acoustic pulse recognition, and surface acoustic wave technologies. Additionally or alternatively, the user interface (832) may include a step switch or foot pedal.

In some embodiments, an output device of the user interface (832) may include one or more of a display device and audio device. The display device may include at least one of a light emitting diode (LED), liquid crystal display (LCD), electroluminescent display (ELD), plasma display panel (PDP), thin film transistor (TFT), and organic light emitting diodes (OLED). An audio device may audibly output patient data, sensor data, system data, other data, alarms, warnings, and/or the like. The audio device may include at least one of a speaker, piezoelectric audio device, magnetostrictive speaker, and/or digital speaker. In one embodiment, the audio device may output an audible warning upon detection of a fault in the signal generator (810) and/or ablation device (840).

In some embodiments, the signal generator (810) may be mounted on a trolley or cart. In some embodiments, the user interface (832) may be formed in the same or different housing as the signal generator (810). The user interface (832) may be mounted to any suitable object, such as furniture (e.g., a bed rail), a wall, a ceiling, or may be self-standing. In some embodiments, the input device may include a wired and/or wireless transmitter configured to transmit a control signal to a wired and/or wireless receiver of the signal generator (810).

In some embodiments, the systems described herein may include one or more sterile coverings configured to create a sterile barrier around portions of the system (800). In some embodiments, the system (800) may include one or more sterile coverings to form a sterile field. For example, a sterile covering may be placed between the ablation device(s) and the patient, forming a barrier between an interior, non-sterile side including the patient, signal generator, and ablation devices and an exterior, sterile side including the operator. Additionally or alternatively, components of the system (800) may be sterilizable. The sterile covering may include, for example, a sterile drape configured to cover at least a portion of a system component. In one embodiment, a sterile covering (e.g., sterile drape) may be configured to create a sterile barrier with respect to a user interface (832) of the system (800). The sterile drape may be clear and allow an operator to visualize and manually manipulate the user interface (832). The sterile covering may conform tightly around one or more system components or may drape loosely so as to allow components to be adjusted within the sterile field.

Ablation Device

The systems described here may include one or more multi-electrode ablation devices configured to ablate tissue for treating Barrett's Esophagus. Generally, the ablation devices may include a set of metallic electrodes. The electrodes may also be generally atraumatic so as to decrease the risk of damage to tissue through laceration and puncture. For example, the edges of the electrodes may be rounded to reduce tissue damage and to increase the uniformity of the electric field generated at a central portion and a peripheral portion of the electrodes. In order to deliver the pulse waveforms generated by the signal generator, one or more electrodes of the ablation device may have an insulated electrical lead configured for sustaining a voltage potential of at least about 700 V without dielectric breakdown of its corresponding insulation. In some embodiments, the insulation on each of the electrical leads may sustain an electrical potential difference of between about 200 V to about 1,000 V across its thickness without dielectric breakdown, including all values and sub-ranges in between. The electrodes may be independently addressable such that each electrode may be controlled (e.g., deliver energy) independently of any other electrode of the device. In this manner, the electrodes may deliver different energy waveforms with different timing synergistically for electroporation of tissue.

The electrodes may, for example, be connected to an insulated electrical lead leading to a handle to receive pulse waveforms generated by a signal generator as discussed above with respect to FIG. 8.

FIG. 1 is a side view of an embodiment of an ablation device (100) including a first catheter (110) (e.g., outer catheter shaft) at a proximal end of the device (100), a distal cap (114) of the device (100), and a set of splines (120) coupled thereto. The first catheter (110) may define a longitudinal axis (140) and a lumen therethrough. The distal cap (114) may include an atraumatic shape to reduce trauma to tissue. A proximal end (122) of the set of splines (120) may be coupled to a distal end of the first catheter (110), and a distal end (126) of the set of splines (120) may be tethered to the distal cap (114) of the device (100). A second catheter (112) (e.g., inner catheter shaft) may be slidably disposed within a lumen of the first catheter (110) so as to extend from a distal end of the first catheter lumen. The second catheter (112) may have a diameter smaller than a diameter of the first catheter (110). A distal end of the second catheter (112) may be coupled to the distal cap (114).

Each spline (120) of the ablation device (100) may include one or more electrodes (130) formed on a surface of the spline (120). In some embodiments, each electrode on a spline may be independently addressable, while in other embodiments one or more subsets of electrodes on a spline may be electrically wired together. Each electrode (130) may include an insulated electrical lead configured to sustain a voltage potential of at least about 700 V without dielectric breakdown of its corresponding insulation. Each spline (120) may include the insulated electrical leads of each electrode (130) formed in a body of the spline (120) (e.g., within a lumen of the spline (120)). FIG. 1 illustrates a set of splines where each spline (120) includes a set of electrodes (130) having about the same size, shape, and spacing as the electrodes (130') of an adjacent spline. In other embodiments, the size, shape, and spacing of the electrodes (130, 130') may differ.

The ablation device (100) may be configured for delivering a set of voltage pulse waveforms using a set of electrodes (130) to ablate tissue and electrically isolate one or more regions of the esophagus (150). In some of these embodiments, the ablation device (100) may be transformed from a first configuration to a second configuration such that the splines (120) of the ablation device (100) expand outward to allow the electrodes (130, 130') to contact esophageal tissue such as at an inferior portion of the esophagus (150) (e.g., towards a distal end of the device (100)).

At least a portion of the set of splines (120) may include a flexible curvature. For example, a proximal region (122) and a distal region (126) of each spline (120) may be more flexible than an intermediate region (124) disposed therebetween. The set of splines (120) may form a delivery assembly at a distal portion of the ablation device (100) and may be configured to transform between a first configuration where the set of splines (120) are arranged generally parallel to the longitudinal axis (140) of the ablation device (100) and a second configuration where the set of splines (120) bow radially outward from a longitudinal axis (140) of the ablation device (100) to form a basket-like shape. In the second configuration, as best illustrated in FIG. 1, each intermediate portion (124) of the set of splines (120) is biased away from and (in some instances) generally parallel to the longitudinal axis (140). In some embodiments, in the second configuration, each intermediate portion (124) of the set of splines (120) may be biased farther away from the longitudinal axis (140) relative to the respective intermediate portion (124) in the first configuration. In this manner, the splines (120) may increase contact with an esophageal wall and more easily conform to the geometry of the esophagus (150). In some embodiments, the proximal region (122) and the distal region (126) of each spline (120) may bend more than the relatively stiff intermediate region (124) of the spline (120). For example, the intermediate region (124) of each spline (120) may have a bending modulus that is at least about 50% larger than the bending modulus of the distal region (126) and proximal region (122) of the spline (120). As shown in FIG. 1, the intermediate regions (124) and electrodes (130) in a second configuration may be generally parallel to esophageal tissue (150) along a length of the second catheter (112) and may thus promote contact between the esophageal tissue and electrode (130). In some embodiments, at least one electrode of the set of electrodes (130) may be disposed substantially within the intermediate region (124) of each spline (120).

In some embodiments, at least a portion of the set of splines (120) may be biased to form an expanded configuration. For example, the second catheter (112) and corresponding set of splines (120) may be slidably disposed within a lumen of the first catheter (110) such that the splines form a first (e.g., compact) configuration. When the second catheter (112) is advanced out of a distal end of first catheter (110), the set of splines (120) may naturally bias (e.g., deploy) towards the expanded configuration such as shown in FIG. 1. At least the distal region (126) of the set of splines (120) form a predetermined angle relative to the longitudinal axis (140). For example, the distal region (126) of the splines (120) may form an angle in the range of between about 20 degrees and about 75 degrees when fully deployed. In some embodiments, the proximal region (122) of each spline (120) may bend more than the relatively stiff intermediate region (124) of the spline (120). For example, the bending modulus of the intermediate region (124) of the splines (120) may be at least 50% larger than the bending modulus of the proximal region (122) of the splines (120).

In other embodiments, the "basket" of splines may have an asymmetric shape along the catheter length, so that one end (say the distal end) of the basket is more bulbous than the other end (say the proximal end) of the basket. The delivery assembly may be advanced through the esophagus (150) in the first configuration and transformed to the second configuration to be disposed in contact with esophageal tissue prior to delivering a pulse waveform. In some embodiments, the ablation device (100) may be configured to be slidably disposed within a lumen of an endoscope and/or sheath (not shown). In some embodiments, a sheath may be coupled to the endoscope.

In some of these embodiments, a handle (not shown) may be coupled to the set of splines (120) and the handle configured for affecting transformation of the set of splines (120) between the first configuration and the second configuration. In some embodiments, actuation of one or more knobs, wheels, sliders, pull wires, and/or other control mechanisms in the handle may result in translation of the second catheter (112) relative to the first catheter (110) and result in bending of the splines (120). In some embodiments, the electrical leads of at least two electrodes of the set of electrodes (130) may be electrically coupled at or near a proximal portion of the ablation device (100), such as, for example, within the handle. For example, the handle may be configured to translate the second catheter (112) and distal cap (114) relative to the first catheter (110), thereby actuating the set of splines (120) coupled to the distal cap (114) and causing them to bend, as shown in FIG. 1. The distal ends of the splines (120) may be fixed to the distal cap (114) and/or first catheter (110) thereby generating buckling of the splines (120) resulting in a bending motion of the splines (120), for example, as the distal cap (114) and second catheter (112) are pulled back relative to the first catheter (110). In some embodiments, a distal end (126) of the set of splines (120) tethered to the distal cap (114) may be translated by up to about 60 mm along the longitudinal axis of the ablation device (100) to actuate this change in configuration. In other words, translation of an actuating member of the handle may bend the set of splines (120). In some embodiments, each spline of the set of splines (120) in the second configuration may be biased laterally away from the longitudinal axis (140) of the second catheter (112) by up to about 35 mm. For example, the set of splines (120) in the second configuration may form a shape with an effective cross-sectional diameter at its largest portion of between about 10 mm and about 35 mm. In the second configuration, the set of splines may have a length between about 15 mm and about 50 mm.

In one embodiment, each of the electrodes (130) on a spline may be configured as an anode while each of the electrodes (130') on a different spline may be configured as a cathode. For example, the set of electrodes on adjacent splines may have opposite polarities. In another embodiment, the electrodes (130) on one spline may alternate between an anode and cathode with the electrodes (130') of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (130) may be electrically wired together within the spline (120), while in alternate embodiments they may be wired together in the handle of the device (100), so that these electrodes (130) are at the same electric potential during ablation. In other embodiments, the size, shape, and spacing of the electrodes (130) may differ as well. As another example, the splines (120) may be activated sequentially in a clockwise or counter-clockwise manner. As another example, the cathode splines may be activated sequentially along with respective sequential anode spline activation until ablation is completed. In embodiments where electrodes (130) on a given spline (120) are wired separately, the order of activation within the electrode (130) of each spline (120) may be varied as well. For example, the electrodes (130) in a spline may be activated all at once or in a predetermined sequence.

In some embodiments where the electrodes may be independently addressable, the electrodes may be energized in any sequence using any pulse waveform sufficient to ablate tissue by irreversible electroporation. For example, the activated pairs of electrodes may deliver hierarchical pulse waveforms, as discussed in further detail below. It should be appreciated that the size, shape, and spacing of the electrodes on and between the splines may be configured to deliver energy to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (120) may include a polymer and define a lumen so as to form a hollow tube. The set of splines (120) of the ablation device (100) may each have a diameter between about 1.0 mm to about 4.0 mm. The set of electrodes (130) of the ablation device (100) may have a diameter between about 1.0 mm to about 4.0 mm and a length between about 0.2 mm to about 8.0 mm.

The ablation device (100) may include any number of splines, for example, 2, 3, 4, 5, 6, 7, 8, 9, 10, 12, 14, 16, or more splines, including all values and sub-ranges in between. In some embodiments, the ablation device (100) may include 3 to 16 splines. For example, the ablation device (100) may include from 3 to 14 splines.

Each of the splines of the set of splines (130) may include respective electrodes (130) having an atraumatic shape to reduce trauma to tissue. For example, the electrodes (130) may have an atraumatic shape including a rounded, flat, curved, and/or blunted portion configured to contact esophageal tissue. In some embodiments, the electrodes (130) may be located along any portion of the spline (120) distal to the first catheter (110). The electrodes (130) may have the same or different sizes, shapes, and/or location along respective splines. The ablation device (100) may include any number of electrodes, for example, 2, 3, 4, 5, 6, 7, 8, 9, 10, 12, or more electrodes per spline, including all values and sub-ranges in between. In some embodiments, the ablation device (100) may include 2 to 12 electrodes per spline.

Figure 2:
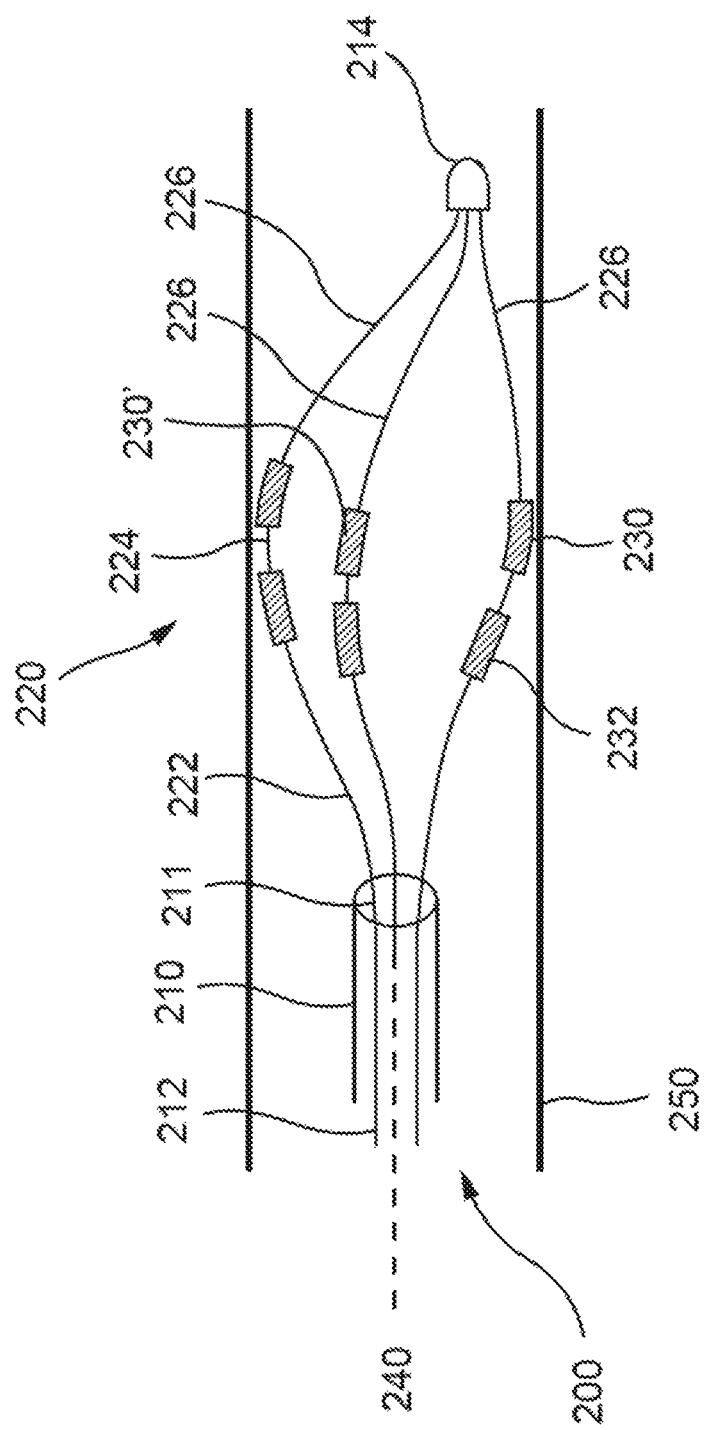
FIG. 2 is a side view of an ablation device disposed in an esophagus, according to other embodiments.

FIG. 2 is a side view of an embodiment of an ablation device (200) including a first catheter (210) (e.g., outer catheter shaft) at a proximal end of the device (200), a distal cap (214) of the device (200), and a set of splines (220) coupled thereto. The first catheter (210) may define a longitudinal axis (240) and a lumen therethrough. The distal cap (214) may include an atraumatic shape to reduce trauma to tissue. A second catheter (212) (e.g., inner catheter shaft) may be slidably disposed within a lumen of the first catheter (210) so as to extend from a distal end of the first catheter lumen. The second catheter (212) may have a diameter smaller than a diameter of the first catheter (210). A proximal end (222) of the set of splines (220) may be coupled to a distal end of the second catheter (212), and a distal end (226) of the set of splines (220) may be tethered to the distal cap (214) of the device (200).

Each spline (220) of the ablation device (200) may include one or more electrodes (230) formed on a surface of the spline (220). Each electrode (230) may include an insulated electrical lead configured to sustain a voltage potential of at least about 700 V without dielectric breakdown of its corresponding insulation. Each spline (220) may include the insulated electrical leads of each electrode (230) formed in a body of the spline (220) (e.g., within a lumen of the spline (220)). FIG. 2 illustrates a set of splines where each spline (220) includes a set of electrodes (230) having about the same size, shape, and spacing as the electrodes (230') of an adjacent spline. In other embodiments, the size, shape, and spacing of the electrodes (230, 230') may differ.

The ablation device (200) may be configured for delivering a set of voltage pulse waveforms using a set of electrodes (230) to ablate tissue in one or more regions of the esophagus (250). In some of these embodiments, the ablation device (200) may be transformed from a first configuration to a second configuration such that the splines (220) of the ablation device (200) expand outward to allow the electrodes (230, 230') to contact esophageal tissue such as at an inferior portion of the esophagus (250) (e.g., towards a distal end of the device (200)).

At least a portion of the set of splines (220) may bias towards a predetermined curvature. The set of splines (220) may form a delivery assembly at a distal portion of the ablation device (200) and may be configured to transform between a first configuration where the set of splines (220) are arranged generally parallel to the longitudinal axis (240) of the ablation device (200) and a second configuration where the set of splines (220) bow radially outward from a longitudinal axis (240) of the ablation device (200) to form a basket-like shape. In the second configuration, the set of splines (220) and the distal cap (214) are biased away from the longitudinal axis (240). In this manner, the splines (220) may more easily conform to the geometry of the esophagus (250). In some embodiments, a proximal region (222) of each spline (220) may be more flexible than an intermediate region (224) and a distal region (226), where the intermediate region (224) is disposed between the proximal region (222) and distal region (226). For example, the bending modulus of the intermediate region (224) of the splines may be at least about 50% larger than the bending modulus of the proximal region (222) of the splines (220). This may allow the distal region (226) and intermediate region (224) to bias towards a predetermined shape when advanced out of a distal end (211) of the first catheter (210). In some embodiments, the distal region (226) may be substantially linear (as shown FIG. 2) or may be substantially curvilinear.

In some embodiments, the intermediate regions (224) and electrodes (230) in a second configuration may be in close proximity and/or in contact with esophageal tissue (250). In some embodiments, at least one electrode of the set of electrodes (230) may be disposed substantially within the intermediate region (224) of each spline (220). Each spline of the set of splines (220) may have different degrees of stiffness such that the set of splines (220) in the second configuration are non-symmetrical. For example, FIG. 2 shows the set of splines (220) in the second configuration forming a curvature such that the distal cap (214) may be biased away from the longitudinal axis (240). That is, the distal cap (214) may be biased closer to a specific side of the esophagus (250). The distal cap (214) in FIG. 2 is biased below the longitudinal axis (240) while the distal cap (114) in FIG. 1 is disposed along the longitudinal axis (140).

In some embodiments, at least a portion of the set of splines (220) may be biased to form a second (e.g., expanded) configuration. For example, the set of splines (220) may be slidably disposed within a lumen of the first catheter (210) such that a delivery assembly may form a first (e.g., compact configuration). When the delivery assembly is advanced out of a distal end (211) of first catheter (210), the set of splines (220) may naturally bias (e.g., deploy) towards the second (e.g., expanded) configuration such as shown in FIG. 2. At least the distal region (226) of the set of splines (220) form a predetermined angle relative to the longitudinal axis (240). In some embodiments, the proximal region (222) of each spline (220) may be more flexible than the relatively stiffer intermediate region (224) and distal region (226) of the spline (220).

In other embodiments, the "basket" of splines may have an asymmetric shape along the catheter length, so that one end (say the distal end) of the basket is more bulbous than the other end (say the proximal end) of the basket. The delivery assembly may be advanced through the esophagus (250) in the first configuration and transformed to the second configuration to be disposed in contact with esophageal tissue prior to delivering a pulse waveform. In some embodiments, the ablation device (200) may be configured to be slidably disposed within a lumen of an endoscope and/or sheath (not shown). In some embodiments, a sheath may be coupled to the endoscope.

In some of these embodiments, a handle (not shown) may be coupled to the set of splines (220) and the handle configured for affecting transformation of the set of splines (220) between the first configuration and the second configuration. In some embodiments, actuation of one or more knobs, wheels, sliders, pull wires, and/or other control mechanisms in the handle may result in translation of the second catheter (212) relative to the first catheter (210) and result in bending of the splines (220). In some embodiments, the electrical leads of at least two electrodes of the set of electrodes (230) may be electrically coupled at or near a proximal portion of the ablation device (200), such as, for example, within the handle. For example, the handle may be configured to translate the second catheter (212) and distal cap (214) relative to the first catheter (210), thereby actuating the set of splines (220) coupled to the distal cap (214) and causing them to deploy, as shown in FIG. 2. The distal ends of the splines (220) may be fixed (e.g., tethered) to the distal cap (214). In some embodiments, a distal end (226) of the set of splines (220) may be translated by up to about 60 mm along the longitudinal axis (240) of the ablation device (200) to actuate this change in configuration. In other words, translation of an actuating member of the handle may bend the set of splines (220). In some embodiments, each spline of the set of splines (220) may be biased laterally away from the longitudinal axis (240) of the second catheter (212) by up to about 35 mm. For example, the set of splines (220) in the second configuration may form a shape with an effective cross-sectional diameter at its largest portion of between about 10 mm and about 35 mm. In some configurations, the set of splines (220) may have a length between about 15 mm and about 50 mm.

In one embodiment, each of the electrodes (230) on a spline may be configured as an anode while each of the electrodes (230') on a different spline may be configured as a cathode. That is, the set of electrodes on adjacent splines may have opposite polarities. In another embodiment, the electrodes (230) on one spline may alternate between an anode and cathode with the electrodes (230') of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (230) may be electrically wired together within the spline (220), while in alternate embodiments they may be wired together in the handle of the device (200), so that these electrodes (230) are at the same electric potential during ablation. In other embodiments, the size, shape, and spacing of the electrodes (230) may differ as well. As another example, the splines (220) may be activated sequentially in a clockwise or counter-clockwise manner. As another example, the cathode splines may be activated sequentially along with respective sequential anode spline activation until ablation is completed. In embodiments where electrodes (230) on a given spline (220) are wired separately, the order of activation within the electrode (230) of each spline (220) may be varied as well. For example, the electrodes (230) in a spline may be activated all at once or in a predetermined sequence.

In some embodiments, the electrodes may be independently addressable, and the electrodes may be energized in any sequence using any pulse waveform sufficient to ablate tissue by irreversible electroporation. It should be appreciated that the size, shape, and spacing of the electrodes on and between the splines may be configured to deliver energy to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (220) may include a polymer and define a lumen so as to form a hollow tube. The set of splines (220) of the ablation device (200) may have a diameter between about 1.0 mm to about 4.0 mm. The set of electrodes (230) of the ablation device (200) may have a diameter between about 1.0 mm to about 4.0 mm and a length between about 0.2 mm to about 5.0 mm.

The ablation device (200) may include any number of splines, for example, 2, 3, 4, 5, 6, 7, 8, 9, 10, 12, 14, 16, or more splines, including all values and sub-ranges in between. In some embodiments, the ablation device (200) may include 3 to 16 splines. For example, the ablation device (200) may include 3 to 14 splines.

Each of the splines of the set of splines (230) may include respective electrodes (230) having an atraumatic shape to reduce trauma to tissue. For example, the electrodes (230) may have an atraumatic shape including a rounded, flat, curved, and/or blunted portion configured to contact esophageal tissue. In some embodiments, the electrodes (230) may be located along any portion of the spline (220) distal to the first catheter (210). The electrodes (230) may have the same or different sizes, shapes, and/or location along respective splines. The electrodes (230) may have the same or different sizes, shapes, and/or location along respective splines. The ablation device (200) may include any number of electrodes, for example, 2, 3, 4, 5, 6, 7, 8, 9, 10, 12, or more electrodes per spline, including all values and sub-ranges in between. In some embodiments, the ablation device (200) may include 2 to 12 electrodes per spline.

Figure 3A:
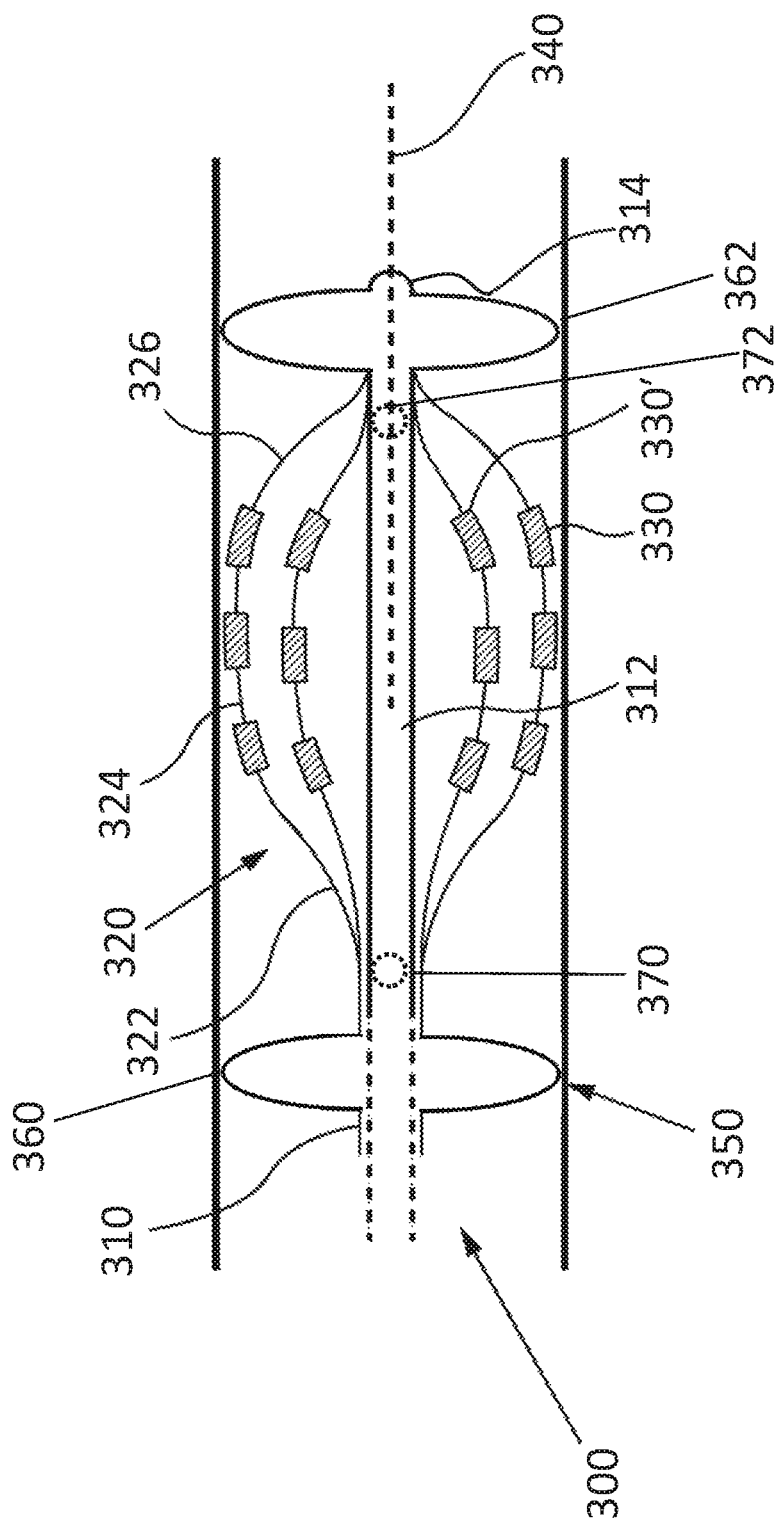
FIG. 3A is a side view of an ablation device disposed in an esophagus, according to other embodiments.
Figure 3B:
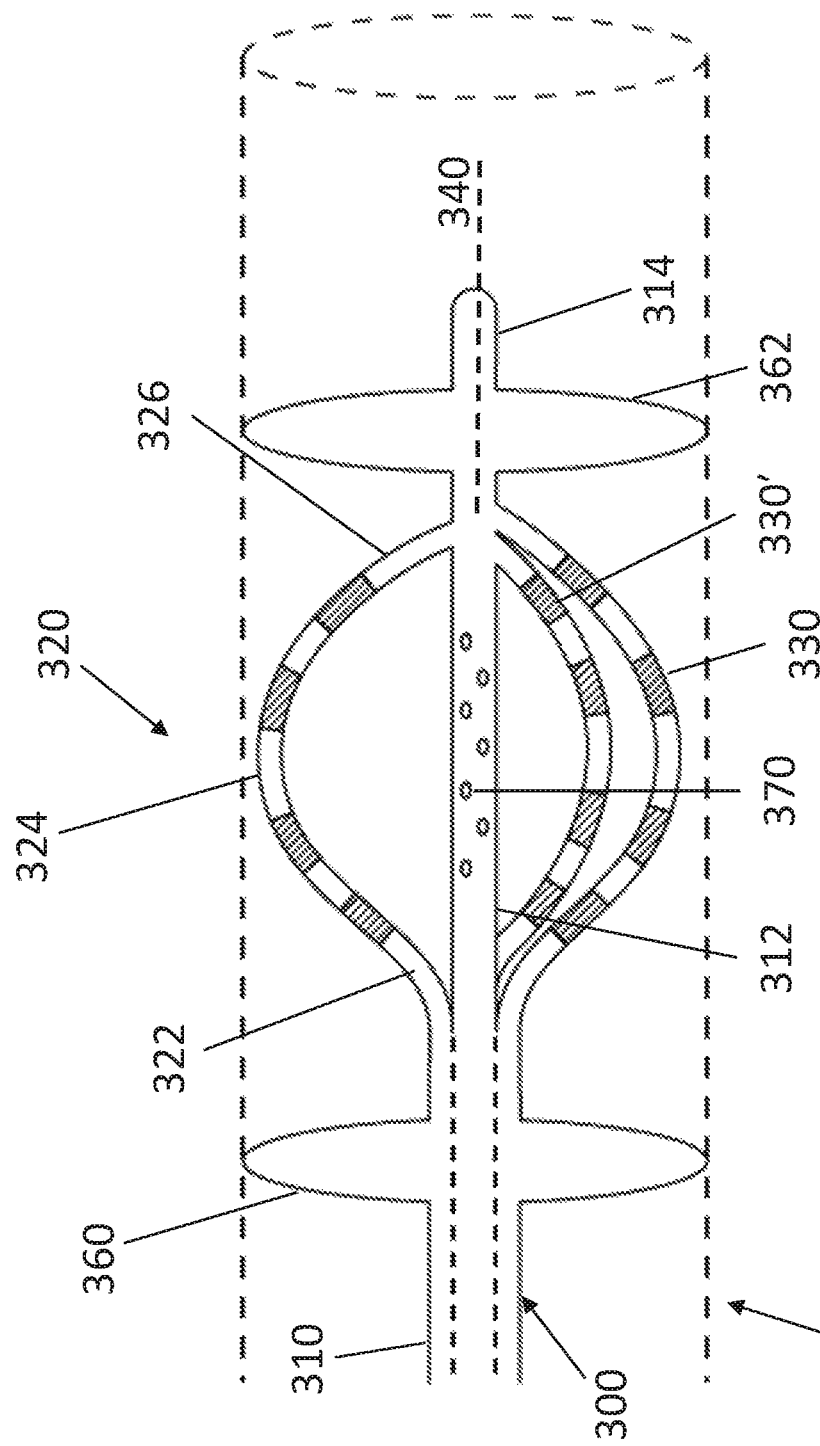
FIG. 3B is a side view of an ablation device disposed in an esophagus, according to other embodiments.

In some embodiments, an ablation device may include one or more balloons that may be inflated by infusion of a fluid such as saline. FIGS. 3A-3B depict an embodiment of an ablation device (300) (e.g., structurally and/or functionally similar to the ablation device (100)) disposed in an esophagus (150). The ablation device (300) may include a first balloon (360) and a second balloon (362) which may be configured to be disposed in a lumen of an esophagus (350). While described in detail herein for FIGS. 3A-3B, it is understood that a set of balloons may be coupled to any of the ablation devices described herein. For example, a balloon may be disposed proximal and distal to a set of electrodes for any of the ablation devices described herein.

FIGS. 3A-3B are side views of an embodiment of the ablation device (300) including a first catheter (310) (e.g., outer catheter shaft) at a proximal end of the device (300), a distal cap (314) of the device (300), and a set of splines (320) coupled thereto. The first catheter (310) may define a longitudinal axis (340) and a lumen therethrough. The distal cap (314) may include an atraumatic shape to reduce trauma to tissue. A proximal end (322) of the set of splines (320) may be coupled to a distal end of the first catheter (310), and a distal end (326) of the set of splines (320) may be tethered to the distal cap (314) of the device (300). A second catheter (312) (e.g., inner catheter shaft) may be slidably disposed within a lumen of the first catheter (310) so as to extend from a distal end of the first catheter lumen. The second catheter (312) may have a diameter smaller than a diameter of the first catheter (310). A distal end of the second catheter (312) may be coupled to the distal cap (314).

A distal end of the first catheter (310) may include a first balloon (360) and a distal end of the second catheter (312) may include a second balloon (372). The first balloon (360) and the second balloon (362) may each be configured to transform between a compact (e.g., deflated) configuration where the balloons (360, 362) may be advanced within a lumen of the esophagus and an expanded (e.g., inflated) configuration where the balloons (360, 362) may contact and/or apply force to the esophagus (350). For example, the balloons (360, 362) may be inflated when positioned at an inferior portion of the esophagus (350), as shown in FIGS. 3A-3B. In other embodiments the balloons (360, 362) may be disposed at any location along a length of the ablation device (300) distal and/or proximal to the set of splines (320). The set of splines (320) may be separated from the balloons (360, 362) by a distance of between about 1 mm and about 20 mm.

In some embodiments, the first balloon (360) and the second balloon (362) may be filled with any suitable fluid such as, for example, saline. The first balloon (360) and the second balloon (362) may be electrically isolated from each other. In some embodiments, the first balloon (360) and the second balloon (362) in the expanded configuration may form a shape with an effective cross-sectional diameter at its largest portion of between about 10 mm and about 35 mm. The inflated balloons (360, 362) may serve to stabilize and/or fix the position of the ablation device (300) relative to the esophagus (350). The balloons (360, 362) in the expanded configuration may form a seal against the esophagus to form a closed chamber within the esophagus (350).

In some embodiments, the second catheter (312) may include a set of fluid openings configured to allow saline to be injected into and/or suctioned out of a space between the first balloon (360) and the second balloon (362). For example, the second catheter (312) may define a first set of openings (370) proximal to the set of electrodes (330) and a second set of openings (372) distal to the set of electrodes (330). In some embodiments, the second catheter (312) may define a conducting fluid lumen coupled to the set of openings (370, 372). The set of openings (370, 372) may be configured to increase a conduction volume encompassing the set of electrodes (330) using electrically conducting fluid. Additional sets of fluid openings may be defined in the second catheter (312) as desired. For example, fluid openings may be disposed underneath the set of splines (320). Infusing the closed chamber formed between the inflated balloons (360, 362) and the esophagus may aid electrical conduction between the set of electrodes (330) and esophageal tissue (350) even when one or more electrodes (330) are not in direct contact with tissue (350). In some embodiments, a first catheter (310) may define a set of fluid openings flow-coupled to a conducting fluid lumen. Conducting fluid may be infused and/or removed from a body cavity using the set of fluid openings and conducting fluid lumen.

Each spline (320) of the ablation device (300) may include one or more electrodes (330) formed on a surface of the spline (320). Each electrode (330) may include an insulated electrical lead configured to sustain a voltage potential of at least about 700 V without dielectric breakdown of its corresponding insulation. Each spline (320) may include the insulated electrical leads of each electrode (330) formed in a body of the spline (320) (e.g., within a lumen of the spline (320)). FIGS. 3A-3B illustrate a set of splines where each spline (320) includes a set of electrodes (330) having about the same size, shape, and spacing as the electrodes (330') of an adjacent spline. In other embodiments, the size, shape, and spacing of electrodes (330, 330') may differ.

The ablation device (300) may be configured for delivering a set of voltage pulse waveforms using a set of electrodes (330) to ablate tissue in one or more regions of the esophagus (350). In some of these embodiments, the set of splines (320) may be transformed from a first configuration to a second configuration such that the splines (320) of the ablation device (300) expand outward to allow the electrodes (330, 330') to be in close proximity and/or contact with esophageal tissue such as at an inferior portion of the esophagus (350) (e.g., towards a distal end of the device (300)). The set of balloons (360, 362) may be transformed from a compact configuration to an expanded configuration such that the balloons (360, 362) expand radially to contact the esophageal tissue. In some embodiments, a conducting fluid such as saline may be injected into the space between the set of balloons (360, 362) via a set of fluid openings. The conducting fluid in contact with one or more of the esophagus (350) and set of electrodes (320) may aid tissue ablation. A set of voltage pulse waveforms may thereafter be applied by the set of electrodes to the esophageal tissue (350).

At least a portion of the set of splines (320) may include a flexible curvature. For example, a proximal region (322) and a distal region (326) of each spline (320) may be more flexible than an intermediate region (324) disposed therebetween. The set of splines (320) may form a delivery assembly at a distal portion of the ablation device (300) and may be configured to transform between a first configuration where the set of splines (320) are arranged generally closer to the longitudinal axis (340) of the ablation device (100) and a second configuration where the set of splines (320) is farther away from from a longitudinal axis (340) of the ablation device (300) to form a basket-like shape. In the second configuration, each intermediate portion (324) of the set of splines (320) is biased away from and may be generally parallel to the longitudinal axis (340). In this manner, the splines (320) may more easily conform to the geometry of the esophagus (350). In some embodiments, the proximal region (322) and the distal region (326) of each spline (320) may bend more than the relatively stiff intermediate region (324) of the spline (320). Therefore, as shown in FIGS. 3A-3B, the intermediate regions (324) and electrodes (330) in a second configuration may be in close proximity and/or in contact with esophageal tissue (350) along a length of the second catheter (312). In some embodiments, at least one electrode of the set of electrodes (330) may be disposed substantially within the intermediate region (324) of each spline (320).

In some embodiments, at least a portion of the set of splines (320) may be biased to form an expanded configuration. For example, the ablation device (300) and corresponding set of splines (320) may be slidably disposed within a lumen of an outer sheath (not shown) such that a delivery assembly may form a first (e.g., compact) configuration. When the delivery assembly is advanced out of a distal end of the outer sheath, the set of splines (320) may naturally bias (e.g., deploy) towards the expanded configuration such as shown in FIGS. 3A-3B. At least the distal region (326) of the set of splines (320) form a predetermined angle relative to the longitudinal axis (340). In some embodiments, the proximal region (322) of each spline (320) may bend more than the relatively stiff intermediate region (324) and distal region (326) of the spline (320).

In other embodiments, the "basket" of splines may have an asymmetric shape along the catheter length, so that one end (say the distal end) of the basket is more bulbous than the other end (say the proximal end) of the basket. The delivery assembly may be advanced through the esophagus (350) in the first configuration and transformed to the second configuration to be disposed in contact with esophageal tissue prior to delivering a pulse waveform. In some embodiments, the ablation device (300) may be configured to be slidably disposed within a lumen of an endoscope and/or sheath (not shown). In some embodiments, a sheath may be coupled to the endoscope.

In some of these embodiments, a handle (not shown) may be coupled to the set of splines (320) and the handle configured for affecting transformation of the set of splines (320) between the first configuration and the second configuration and for affecting transformation of the set of balloons (360, 362) between the compact configuration and the expanded configuration. In some embodiments, actuation of one or more knobs, wheels, sliders, pull wires, and/or other control mechanisms in the handle may result in translation of the second catheter (312) relative to the first catheter (310) and result in bending of the splines (320), inflation/deflation of the set of balloons (360, 362), and/or injection of conduction fluid through the set of openings (370, 372). Additionally or alternatively, in some embodiments, the set of balloons (360, 362) may define a set of openings (370, 372). For example, the set of openings (370, 372) may be disposed on a surface of the first catheter within the set of balloons (360, 362), where the balloon surfaces in turn define a set of pores. This may allow a continuous flow of fluid to inflate the set of balloons (360, 362) and simultaneously inject fluid through the pores on the balloon surfaces into a body cavity to improve conduction in the vicinity of the set of splines (320). In some embodiments, the pores can be formed on that portion of the balloon surface of each balloon (360, 362) that faces the set of splines (320).

In some embodiments, the electrical leads of at least two electrodes of the set of electrodes (330) may be electrically coupled at or near a proximal portion of the ablation device (300), such as, for example, within the handle. For example, the handle may be configured to translate the second catheter (312) and distal cap (314) relative to the first catheter (310), thereby actuating the set of splines (320) coupled to the distal cap (314) and causing them to bend, as shown in FIGS. 3A-3B. The distal ends of the splines (320) may be fixed to the distal cap (314) and/or first catheter (310) thereby generating buckling of the splines (320) resulting in a bending motion of the splines (320), for example, as the distal cap (314) and second catheter (312) are pulled back relative to the first catheter (310). In some embodiments, a distal end (326) of the set of splines (320) tethered to the distal cap (314) may be translated by up to about 60 mm along the longitudinal axis of the ablation device (300) to actuate this change in configuration. In other words, translation of an actuating member of the handle may bend the set of splines (320). In some embodiments, each spline of the set of splines (320) may be biased laterally away from the longitudinal axis (340) of the second catheter (312) by up to about 35 mm. For example, the set of splines (320) in the second configuration may form a shape with an effective cross-sectional diameter at its largest portion of between about 10 mm and about 35 mm. In some configurations, the set of splines (320) may have a length between about 15 mm and about 50 mm.

In one embodiment, each of the electrodes (330) on a spline may be configured as an anode while each of the electrodes (330') on a different spline may be configured as a cathode. That is, the set of electrodes on adjacent splines may have opposite polarities. In another embodiment, the electrodes (330) on one spline may alternate between an anode and cathode with the electrodes (330') of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (330) may be electrically wired together within the spline (320), while in alternate embodiments they may be wired together in the handle of the device (300), so that these electrodes (330) are at the same electric potential during ablation. In other embodiments, the size, shape, and spacing of the electrodes (330) may differ as well. As another example, the splines (320) may be activated sequentially in a clockwise or counter-clockwise manner. As another example, the cathode splines may be activated sequentially along with respective sequential anode spline activation until ablation is completed. In embodiments where electrodes (330) on a given spline (320) are wired separately, the order of activation within the electrode (330) of each spline (320) may be varied as well. For example, the electrodes (330) in a spline may be activated all at once or in a predetermined sequence.

The electrodes may be energized in any sequence using any pulse waveform sufficient to ablate tissue by irreversible electroporation. It should be appreciated that the size, shape, and spacing of the electrodes on and between the splines may be configured to deliver sufficient energy to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (320) may include a polymer and define a lumen so as to form a hollow tube. The set of splines (320) of the ablation device (300) may have a diameter between about 1.0 mm to about 4.0 mm. The set of electrodes (330) of the ablation device (300) may have a diameter between about 1.0 mm to about 4.0 mm and a length between about 0.2 mm to about 5.0 mm.

The ablation device (300) may include any number of splines, for example, 2, 3, 4, 5, 6, 7, 8, 9, 10, 12, 14, 16, or more splines, including all values and sub-ranges in between. In some embodiments, the ablation device (300) may include 3 to 16 splines. For example, the ablation device (300) may include from 3 to 14 splines. The ablation device (300) may include any number of balloons, for example, 1, 2, 3, or more balloons. The set of balloons may each have an atraumatic shape to reduce trauma to tissue. The ablation device (300) may include any number of fluid openings having any suitable size and shape. For example, the balloons may have an atraumatic shape including a rounded, flat, curved, and/or blunted portion configured to contact esophageal tissue. In some embodiments, at a given position along a length of the ablation device (300), a set of balloons may be disposed radially about the longitudinal axis (340) of the ablation device (300). The set of balloons may include a set of seals (e.g., bellows) configured to prevent fluid from leaking out of the set of balloons and into a body cavity.

Each of the splines of the set of splines (330) may include respective electrodes (330) having an atraumatic shape to reduce trauma to tissue. For example, the electrodes (330) may have an atraumatic shape including a rounded, flat, curved, and/or blunted portion configured to contact esophageal tissue. In some embodiments, the electrodes (330) may be located along any portion of the spline (320) distal to the first catheter (310). The electrodes (330) may have the same or different sizes, shapes, and/or location along respective splines. The ablation device (300) may include any number of electrodes, for example, 2, 3, 4, 5, 6, 7, 8, 9, 10, 12, or more electrodes per spline, including all values and sub-ranges in between. In some embodiments, the ablation device (300) may include 2 to 12 electrodes per spline.

Figure 7:
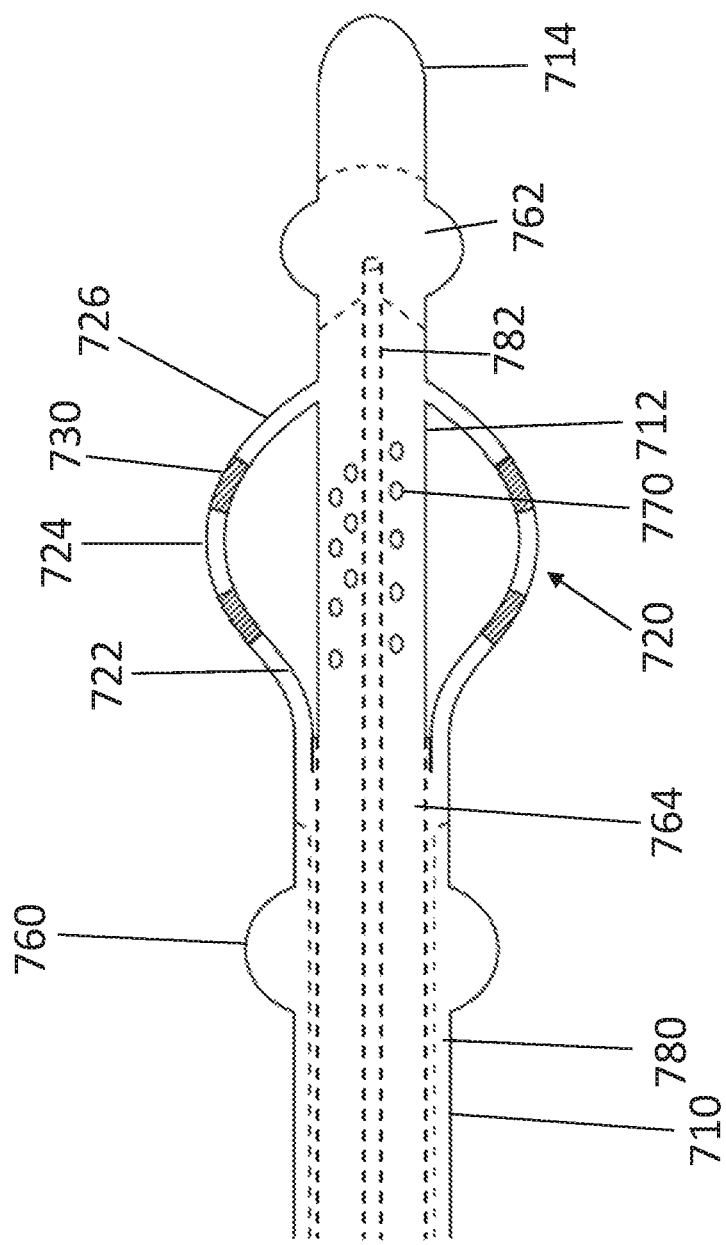
FIG. 7 is a cross-sectional side view of an ablation device disposed in an esophagus, according to other embodiments.

FIG. 7 depicts an embodiment of a balloon ablation device (700) (e.g., structurally and/or functionally similar to the ablation device (300)) disposed in an esophagus. The ablation device (700) may include a first balloon (760) and a second balloon (762) which may be configured to be disposed in a lumen of an esophagus.

An ablation device (700) may include a first catheter (710) (e.g., outer catheter shaft) at a proximal end of the device (700), a distal cap (714) of the device (700), and a set of splines (720) coupled thereto. The first catheter (710) may define a longitudinal axis (740) and a lumen therethrough. The distal cap (714) may include an atraumatic shape to reduce trauma to tissue. A proximal end (722) of the set of splines (720) may be coupled to a distal end of the first catheter (710), and a distal end (726) of the set of splines (720) may be tethered to the distal cap (714) of the device (700). A second catheter (712) (e.g., inner catheter shaft) may be slidably disposed within a lumen of the first catheter (710) so as to extend from a distal end of the first catheter lumen. The second catheter (712) may have a diameter smaller than a diameter of the first catheter (710). A distal end of the second catheter (712) may be coupled to a second balloon (762) and the distal cap (714).

A distal end of the first catheter (710) may include a first balloon (760) and a seal (770), and a distal end of the second catheter (712) may include a second balloon (772). The first balloon (760) and the second balloon (762) may each be configured to transform between a compact (e.g., deflated) configuration where the balloons (760, 762) may be advanced within a lumen of the esophagus and an expanded (e.g., inflated) configuration where the balloons (760, 362) may contact and/or apply force to the esophagus. In other embodiments, the balloons (760, 762) may be disposed at any location along a length of the ablation device (700) distal and/or proximal to the set of splines (720). The set of splines (720) may be separated from the balloons (760, 362) by a distance of between about 1 mm and about 50 mm.

In some embodiments, the first balloon (760) and the second balloon (762) may be filled with any suitable conducting fluid such as, for example, saline. In some embodiments, the first catheter (710) may define a first fluid lumen (780) that may be flow-coupled coupled to the first balloon (760). The second catheter (712) may define a second fluid lumen (782) that may be flow-coupled coupled to the second balloon (762). The first and second fluid lumens (780, 782) may be used to inflate and/or deflate respective first and second balloons (760, 762).

The first balloon (760) and the second balloon (762) may be electrically isolated from each other. In some embodiments, the first balloon (760) and the second balloon (762) in the expanded configuration may form a shape with an effective cross-sectional diameter at its largest portion of between about 10 mm and about 35 mm. The inflated balloons (760, 362) may serve to stabilize and/or fix the position of the ablation device (700) relative to the esophagus (750). The balloons (760, 362) in the expanded configuration may form a seal against the esophagus to form a closed chamber within the esophagus (750).

In some embodiments, the second catheter (712) may include a set of fluid openings configured to allow saline to be injected into and/or suctioned out of a space such as a body cavity. For example, the second catheter (712) may define a set of openings (770) along a length of the set of splines (720). In some embodiments, the second catheter (712) may define a third fluid lumen (764) flow-coupled to the set of openings (770). The set of openings (770) may be configured to increase a conduction volume encompassing the set of electrodes (730) using electrically conducting fluid. Additional sets of fluid openings may be defined in the second catheter (712) as desired. Infusing an enclosed chamber formed by the inflated balloons (760, 762) and the esophagus may aid electrical conduction between the set of electrodes (730) and esophageal tissue (750) even when one or more electrodes (730) are not in direct contact with tissue (750). Conducting fluid may be infused and/or removed from a body cavity using the set of fluid openings (770) and third fluid lumen (764).

Each spline (720) of the ablation device (700) may include one or more electrodes (730) formed on a surface of the spline (720). Each electrode (730) may include an insulated electrical lead configured to sustain a voltage potential of at least about 700 V without dielectric breakdown of its corresponding insulation. Each spline (720) may include the insulated electrical leads of each electrode (730) formed in a body of the spline (720) (e.g., within a lumen of the spline (720)). FIG. 7 illustrates a set of splines where each spline (720) includes a set of electrodes (730) having about the same size, shape, and spacing as the electrodes of an adjacent spline. In other embodiments, the size, shape, and spacing of the electrodes (730) may differ.

The ablation device (700) may be configured for delivering a set of voltage pulse waveforms using a set of electrodes (730) to ablate tissue. In some of these embodiments, the set of splines (720) may be transformed from a first configuration to a second configuration. The set of balloons (760, 362) may be transformed from a compact configuration to an expanded configuration such that the balloons (760, 362) expand. In some embodiments, a conducting fluid such as saline may be injected into the space between the set of balloons (760, 362) via a set of fluid openings. A set of voltage pulse waveforms may thereafter be applied by the set of electrodes to the esophageal tissue (750).

At least a portion of the set of splines (720) may include a flexible curvature. For example, a proximal region (722) and a distal region (726) of each spline (720) may be more flexible than an intermediate region (724) disposed therebetween. The set of splines (720) may form a delivery assembly at a distal portion of the ablation device (700) and may be configured to transform between a first configuration where the set of splines (720) are arranged generally closer to the longitudinal axis (740) of the ablation device (100) and a second configuration where the set of splines (720) is farther away from a longitudinal axis (740) of the ablation device (700) to form a basket-like shape. In the second configuration, each intermediate portion (724) of the set of splines (720) is biased away from and may be generally parallel to the longitudinal axis (740). In some embodiments, the proximal region (722) and the distal region (726) of each spline (720) may bend more than the relatively stiff intermediate region (724) of the spline (720).

In some embodiments, at least a portion of the set of splines (720) may be biased to form an expanded configuration. For example, the second catheter (712) and corresponding set of splines (720) may be slidably disposed within a lumen of the first catheter (720) such that it may form a first (e.g., compact) configuration. When the second catheter (712) is advanced out of a distal end of the first catheter (710), the set of splines (720) may naturally bias (e.g., deploy) towards the expanded configuration such as shown in FIG. 7.

In some of these embodiments, a handle (not shown) may be coupled to the set of splines (720) and the handle configured for affecting transformation of the set of splines (720) between the first configuration and the second configuration and for affecting transformation of the set of balloons (760, 762) between the compact configuration and the expanded configuration. In some embodiments, actuation of one or more knobs, wheels, sliders, pull wires, and/or other control mechanisms in the handle may result in translation of the second catheter (712) relative to the first catheter (710) and result in bending of the splines (720), inflation/deflation of the set of balloons (760, 762), and/or injection of conduction fluid through the set of openings (770). In some embodiments, the electrical leads of at least two electrodes of the set of electrodes (730) may be electrically coupled at or near a proximal portion of the ablation device (700), such as, for example, within the handle. For example, the handle may be configured to translate the second catheter (712) and distal cap (714) relative to the first catheter (710), thereby actuating the set of splines (720) coupled to the distal cap (714) and causing them to bend, as shown in FIG. 7. The distal ends of the splines (720) may be fixed to the distal cap (714) and/or first catheter (710) thereby generating buckling of the splines (720) resulting in a bending motion of the splines (720), for example, as the distal cap (714) and second catheter (712) are pulled back relative to the first catheter (710). In some embodiments, a distal end (726) of the set of splines (720) tethered to the distal cap (714) may be translated by up to about 60 mm along the longitudinal axis of the ablation device (700) to actuate this change in configuration. In other words, translation of an actuating member of the handle may bend the set of splines (720). In some embodiments, each spline of the set of splines (720) may be biased laterally away from the longitudinal axis (740) of the second catheter (712) by up to about 35 mm. For example, the set of splines (720) in the second configuration may form a shape with an effective cross-sectional diameter at its largest portion of between about 10 mm and about 35 mm. In some configurations, the set of splines (720) may have a length between about 15 mm and about 50 mm.

In one embodiment, each of the electrodes (730) on a spline may be configured as an anode while each of the electrodes (730') on a different spline may be configured as a cathode. That is, the set of electrodes on adjacent splines may have opposite polarities. In another embodiment, the electrodes (730) on one spline may alternate between an anode and cathode with the electrodes (730') of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (730) may be electrically wired together within the spline (720), while in alternate embodiments they may be wired together in the handle of the device (700), so that these electrodes (730) are at the same electric potential during ablation. In other embodiments, the size, shape, and spacing of the electrodes (730) may differ as well. As another example, the splines (720) may be activated sequentially in a clockwise or counter-clockwise manner. As another example, the cathode splines may be activated sequentially along with respective sequential anode spline activation until ablation is completed. In embodiments where electrodes (730) on a given spline (720) are wired separately, the order of activation within the electrode (730) of each spline (720) may be varied as well. For example, the electrodes (730) in a spline may be activated all at once or in a predetermined sequence.

In some embodiments, the electrodes may be independently addressable, and the electrodes may be energized in any sequence using any pulse waveform sufficient to ablate tissue by irreversible electroporation. It should be appreciated that the size, shape, and spacing of the electrodes on and between the splines may be configured to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (720) may include a polymer and define a lumen so as to form a hollow tube. The set of splines (720) of the ablation device (700) may have a diameter between about 1.0 mm to about 4.0 mm. The set of electrodes (730) of the ablation device (700) may have a diameter between about 1.0 mm to about 4.0 mm and a length between about 0.2 mm to about 10 mm.

The ablation device (700) may include any number of splines, for example, 2, 3, 4, 5, 6, 7, 8, 9, 10, 12, 14, 16, or more splines, including all values and sub-ranges in between. In some embodiments, the ablation device (700) may include 3 to 16 splines. For example, the ablation device (700) may include from 3 to 14 splines. The ablation device (700) may include any number of balloons, for example, 1, 2, 3, or more balloons. The set of balloons may each have an atraumatic shape to reduce trauma to tissue. The ablation device (700) may include any number of fluid openings having any suitable size and shape. For example, the balloons may have an atraumatic shape including a rounded, flat, curved, and/or blunted portion configured to contact esophageal tissue. In some embodiments, at a given position along a length of the ablation device (700), a set of balloons may be disposed radially about the longitudinal axis (740) of the ablation device (700). The set of balloons may include a set of seals (e.g., bellows) configured to prevent fluid from leaking out of the set of balloons and into a body cavity.

Each of the splines of the set of splines (730) may include respective electrodes (730) having an atraumatic shape to reduce trauma to tissue. For example, the electrodes (730) may have an atraumatic shape including a rounded, flat, curved, and/or blunted portion configured to contact esophageal tissue. In some embodiments, the electrodes (730) may be located along any portion of the spline (720) distal to the first catheter (710). The electrodes (730) may have the same or different sizes, shapes, and/or location along respective splines. The ablation device (700) may include any number of electrodes, for example, 2, 3, 4, 5, 6, 7, 8, 9, 10, 12, or more electrodes per spline, including all values and sub-ranges in between. In some embodiments, the ablation device (700) may include 2 to 12 electrodes per spline.

Figure 4:
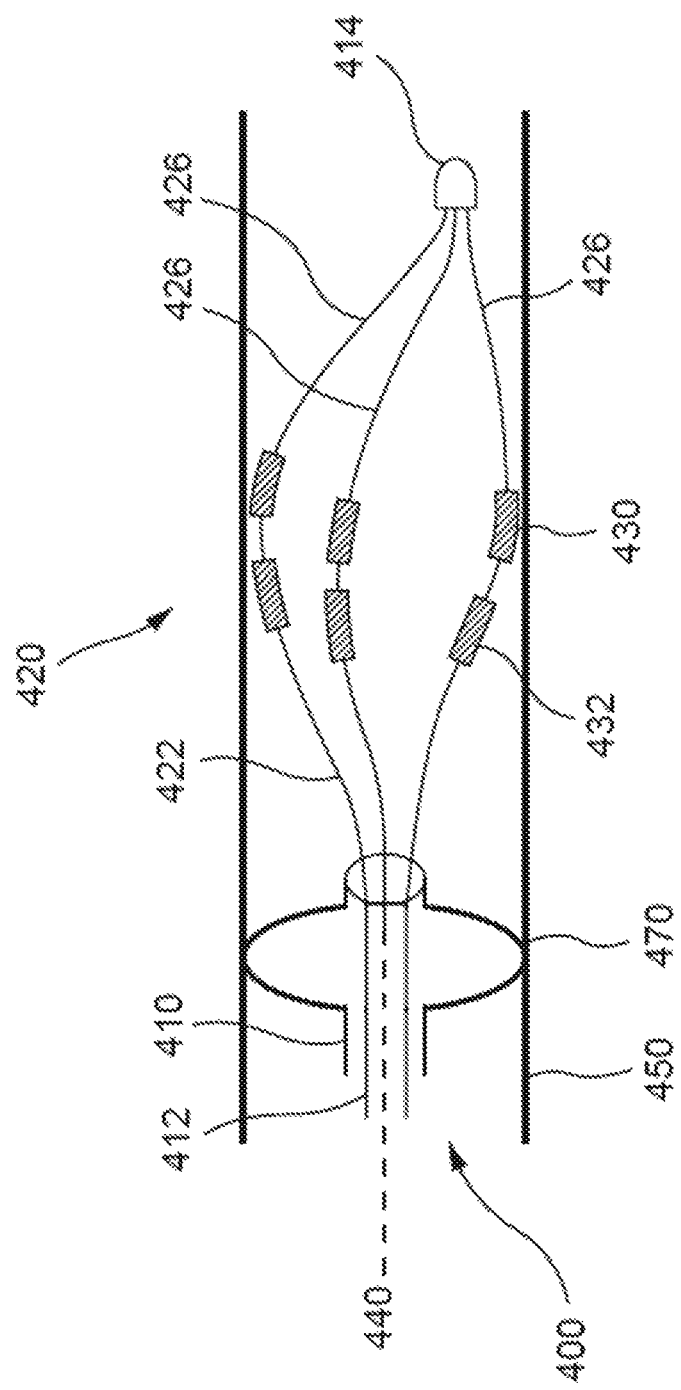
FIG. 4 is a side view of an ablation device disposed in an esophagus, according to other embodiments.

In some embodiments, an ablation device may include one or more balloons for delivering saline to aid electrical conduction while delivering ablation by irreversible electroporation. FIG. 4 depicts an embodiment of a balloon ablation device (400) (e.g., structurally and/or functionally similar to the ablation device (400)) disposed in an esophagus (450). The ablation device (400) may include a first balloon (470) which may be configured to be disposed in a lumen of an esophagus (450).

FIG. 4 is a side view of an embodiment of an ablation device (400) including a first catheter (410) (e.g., outer catheter shaft) at a proximal end of the device (400), a distal cap (414) of the device (400), and a set of splines (420) coupled thereto. The first catheter (410) may define a longitudinal axis (440) and a lumen therethrough. The distal cap (414) may include an atraumatic shape to reduce trauma to tissue. A second catheter (412) (e.g., inner catheter shaft) may be slidably disposed within a lumen of the first catheter (410) so as to extend from a distal end of the first catheter lumen. The second catheter (412) may have a diameter smaller than a diameter of the first catheter (410). A proximal end (422) of the set of splines (420) may be coupled to a distal end of the second catheter (412), and a distal end (426) of the set of splines (420) may be coupled and/or tethered to the distal cap (414) of the device (400).

In some embodiments, the second catheter (412) may include a set of fluid openings configured to allow saline to be injected distal to the first balloon (470) and toward the set of electrodes (430). For example, the second catheter (412) may define a first set of openings (470) proximal to the set of electrodes (430). In some embodiments, the second catheter (412) may define a conducting fluid lumen coupled to the set of openings (470). The set of openings (470) may be configured to irrigate and/or increase a conduction volume encompassing the set of electrodes (430) using conduction fluid. Additional sets of fluid openings may be defined in the first catheter (410) and/or first balloon (460) as desired. For example, fluid openings may be directed towards one or more of the set of electrodes (430). In some embodiments, the balloon (460) may be inflated such that conducting fluid output from the set of fluid openings (470) may fill space distal to the balloon (460), thereby increasing a conduction volume for tissue ablation. In some embodiments, a first catheter (410) may define a set of fluid openings flow-coupled to a conducting fluid lumen.

Each spline (420) of the ablation device (400) may include one or more electrodes (430) formed on a surface of the spline (420). Each electrode (430) or subset of electrodes may include an insulated electrical lead configured to sustain a voltage potential of at least about 700 V without dielectric breakdown of its corresponding insulation. Each spline (420) may include the insulated electrical leads of each electrode (430) formed in a body of the spline (420) (e.g., within a lumen of the spline (420)). FIG. 4 illustrates a set of splines where each spline (420) includes a set of electrodes (430) having about the same size, shape, and spacing as the electrodes of an adjacent spline. In other embodiments, the size, shape, and spacing of the electrodes (430) may differ.

The ablation device (400) may be configured for delivering a set of voltage pulse waveforms using a set of electrodes (430) to ablate tissue in one or more regions of the esophagus (450). In some of these embodiments, the ablation device (400) may be transformed from a first configuration to a second configuration such that the splines (420) of the ablation device (400) expand outward to allow the electrodes (430) to contact esophageal tissue such as at an inferior portion of the esophagus (450) (e.g., towards a distal end of the device (400)). The first balloon (460) may be transformed from a compact configuration to an expanded configuration such that the first balloon (460) expands radially to contact the esophageal tissue. In some embodiments, a conducting fluid such as saline may be injected into the space between the set of balloons (460) via a set of fluid openings. The conducting fluid in contact with one or more of the esophagus (450) and set of electrodes (420) may aid tissue ablation. A set of voltage pulse waveforms may thereafter be applied by the set of electrodes to the esophageal tissue (450).

At least a portion of the set of splines (420) may bias towards a predetermined curvature. The set of splines (420) may form a delivery assembly at a distal portion of the ablation device (400) and may be configured to transform between a first configuration where the set of splines (420) are arranged generally parallel to the longitudinal axis (440) of the ablation device (400) and a second configuration where the set of splines (420) bow radially outward from a longitudinal axis (440) of the ablation device (400) to form a basket-like shape. In the second configuration, the set of splines (420) and the distal cap (414) are biased away from the longitudinal axis (440). In this manner, the splines (420) may more easily conform to the geometry of the esophagus (450). In some embodiments, a proximal region (422) of each spline (420) may be more flexible than an intermediate region (424) and a distal region (426), where the intermediate region (424) is disposed between the proximal region (422) and distal region (426). For example, the bending modulus of the intermediate region (424) may be at least about 50% larger than the bending modulus of the proximal region (422) and the distal region (426). This may allow the distal region (426) and intermediate region (424) to bias towards a predetermined shape when advanced out of a distal end (411) of the first catheter (410). In some embodiments, the distal region (426) may be substantially linear (as shown FIG. 4) or may be substantially curvilinear.

In some embodiments, the intermediate regions (424) and electrodes (430) in a second configuration may be generally parallel to esophageal tissue (450) and may thus promote contact between the esophageal tissue and electrode (430). In some embodiments, at least one electrode of the set of electrodes (430) may be disposed substantially within the intermediate region (424) of each spline (420). Each spline of the set of splines (420) may have different stiffnesses such that the set of splines (420) in the second configuration are non-symmetrical. For example, FIG. 4 shows the set of splines (420) in the second configuration forming a curvature such that the distal cap (414) may be biased away from the longitudinal axis (440). That is, the distal cap (414) may be biased closer to a specific side of the esophagus (450).

In some embodiments, at least a portion of the set of splines (420) may be biased to form a second (e.g., expanded) configuration. For example, the set of splines (420) may be slidably disposed within a lumen of the first catheter (410) such that a delivery assembly may form a first (e.g., compact configuration). When the delivery assembly is advanced out of a distal end (411) of first catheter (410), the set of splines (420) may naturally bias (e.g., deploy) towards the second (e.g., expanded) configuration such as shown in FIG. 4. At least the distal region (426) of the set of splines (420) form a predetermined angle relative to the longitudinal axis (440). In some embodiments, the proximal region (422) of each spline (420) may be more flexible than the relatively stiffer intermediate region (424) and distal region (426) of the spline (420).

In other embodiments, the "basket" of splines may have an asymmetric shape along the catheter length, so that one end (say the distal end) of the basket is more bulbous than the other end (say the proximal end) of the basket. The delivery assembly may be advanced through the esophagus (450) in the first configuration and transformed to the second configuration to be disposed in contact with esophageal tissue prior to delivering a pulse waveform. In some embodiments, the ablation device (400) may be configured to be slidably disposed within a lumen of an endoscope and/or sheath (not shown). In some embodiments, a sheath may be coupled to the endoscope.

In some of these embodiments, a handle (not shown) may be coupled to the set of splines (420) and the handle configured for affecting transformation of the set of splines (420) between the first configuration and the second configuration and for affecting transformation of the first balloon (460) between the compact configuration and the expanded configuration. In some embodiments, actuation of one or more knobs, wheels, sliders, pull wires, and/or other control mechanisms in the handle may result in translation of the second catheter (412) relative to the first catheter (410) and result in bending of the splines (420), inflation/deflation of the first balloon (460), and/or injection of conduction fluid through the set of openings (470). In some embodiments, the electrical leads of at least two electrodes of the set of electrodes (430) may be electrically coupled at or near a proximal portion of the ablation device (400), such as, for example, within the handle. For example, the handle may be configured to translate the second catheter (412) and distal cap (414) relative to the first catheter (410), thereby actuating the set of splines (420) coupled to the distal cap (414) and causing them to deploy, as shown in FIG. 4. The distal ends of the splines (420) may be fixed (e.g., tethered) to the distal cap (414). In some embodiments, a distal end (426) of the set of splines (420) may be translated by up to about 60 mm along the longitudinal axis (440) of the ablation device (400) to actuate this change in configuration. In other words, translation of an actuating member of the handle may bend the set of splines (420). In some embodiments, each spline of the set of splines (420) may be biased laterally away from the longitudinal axis (440) by up to about 35 mm. For example, the set of splines (420) in the second configuration may form a shape with an effective cross-sectional diameter at its largest portion of between about 10 mm and about 35 mm. In the second configuration, the set of splines (420) may have a length between about 15 mm and about 50 mm. In some embodiments, the set of splines (420) may be separated from the first balloon (460) by a distance between about 1 mm and about 12 mm.

In one embodiment, each of the electrodes (430) on a spline may be configured as an anode while each of the electrodes on a different spline may be configured as a cathode. That is, the set of electrodes on adjacent splines may have opposite polarities. In another embodiment, the electrodes (430) on one spline may alternate between an anode and cathode with the electrodes of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (430) may be electrically wired together within the spline (420), while in alternate embodiments they may be wired together in the handle of the device (400), so that these electrodes (430) are at the same electric potential during ablation. In other embodiments, the size, shape, and spacing of the electrodes (430) may differ as well. As another example, the splines (420) may be activated sequentially in a clockwise or counter-clockwise manner. As another example, the cathode splines may be activated sequentially along with respective sequential anode spline activation until ablation is completed. In embodiments where electrodes (430) on a given spline (420) are wired separately, the order of activation within the electrode (430) of each spline (420) may be varied as well. For example, the electrodes (430) in a spline may be activated all at once or in a predetermined sequence.

In some embodiments, the electrodes may be independently addressable, and the electrodes may be energized in any sequence using any pulse waveform sufficient to ablate tissue by irreversible electroporation It should be appreciated that the size, shape, and spacing of the electrodes on and between the splines may be configured to deliver contiguous/transmural energy to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the splines (420) may include a polymer and define a lumen so as to form a hollow tube. The set of splines (420) of the ablation device (400) may have a diameter between about 1.0 mm to about 5.0 mm. The set of electrodes (430) of the ablation device (400) may have a diameter between about 1.0 mm to about 4.0 mm and a length between about 0.2 mm to about 4.0 mm.

The ablation device (400) may include any number of splines, for example, 2, 3, 4, 5, 6, 7, 8, 9, 10, 12, 14, 16, or more splines, including all values and sub-ranges in between. In some embodiments, the ablation device (400) may include 3 to 16 splines. For example, the ablation device (400) may include 3 to 14 splines. The ablation device (400) may include any number of balloons, for example, 1, 2, 3, or more balloons. The set of balloons may each have an atraumatic shape to reduce trauma to tissue. For example, the balloons may have an atraumatic shape including a rounded, flat, curved, and/or blunted portion configured to contact esophageal tissue. The ablation device (400) may include any number of fluid openings having any suitable size and shape. In some embodiments, at a given position along a length of the ablation device (400), a set of balloons may be disposed radially about the longitudinal axis (440) of the ablation device (400).

Each of the splines of the set of splines (430) may include respective electrodes (430) having an atraumatic shape to reduce trauma to tissue. For example, the electrodes (430) may have an atraumatic shape including a rounded, flat, curved, and/or blunted portion configured to contact esophageal tissue. In some embodiments, the electrodes (430) may be located along any portion of the spline (420) distal to the first catheter (410). The electrodes (430) may have the same or different sizes, shapes, and/or location along respective splines. In some embodiments, the electrodes (430) may be located along any portion of the spline (420) distal to the first catheter (410). The electrodes (430) may have the same or different sizes, shapes, and/or location along respective splines. The ablation device (400) may include any number of electrodes, for example, 2, 3, 4, 5, 6, 7, 8, 9, 10, 12, or more electrodes per spline, including all values and sub-ranges in between. In some embodiments, the ablation device (400) may include 2 to 12 electrodes per spline.

Figure 5A:
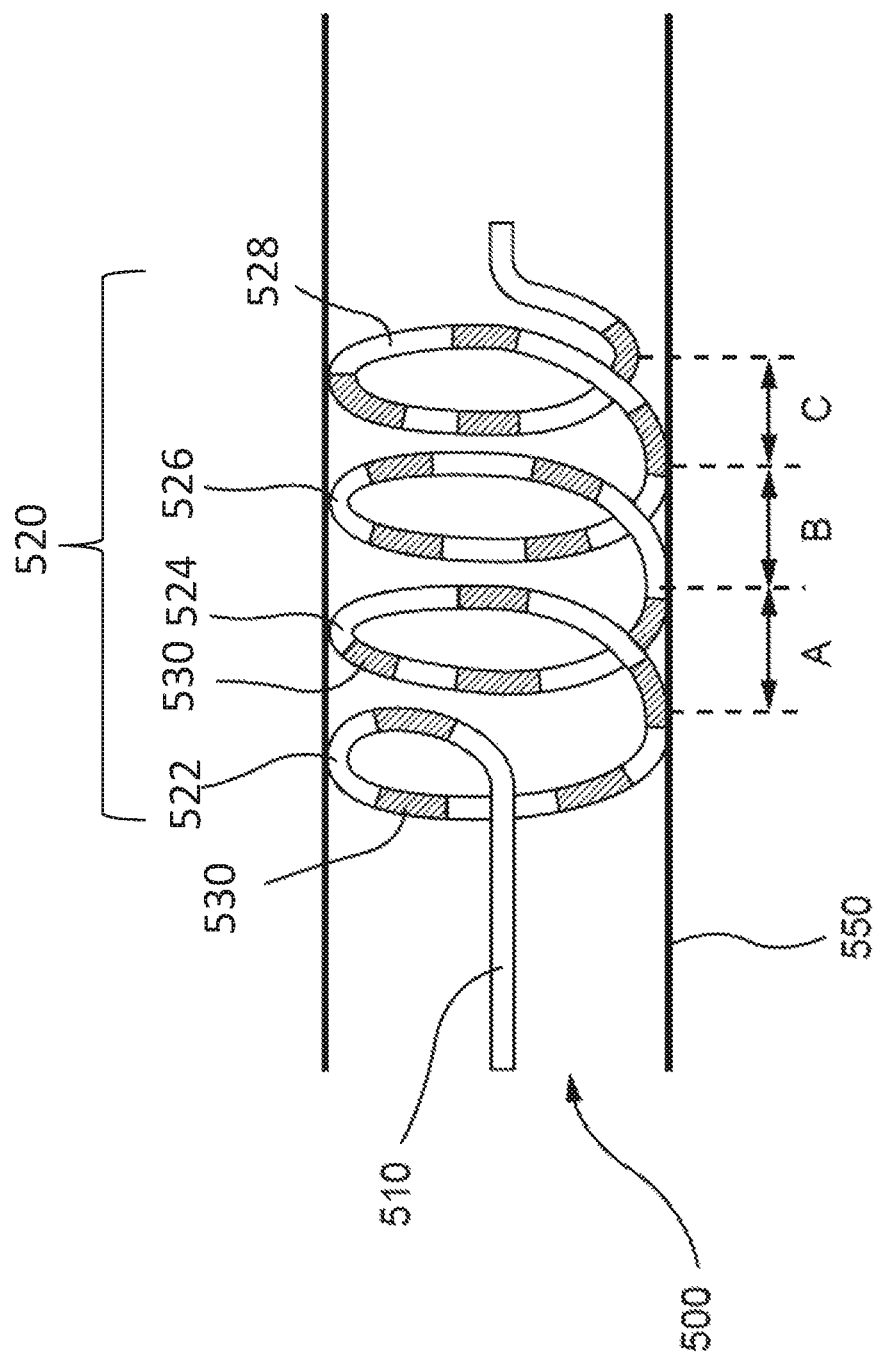
FIG. 5A is a side view of an ablation device disposed in an esophagus according to embodiments.
Figure 5B:
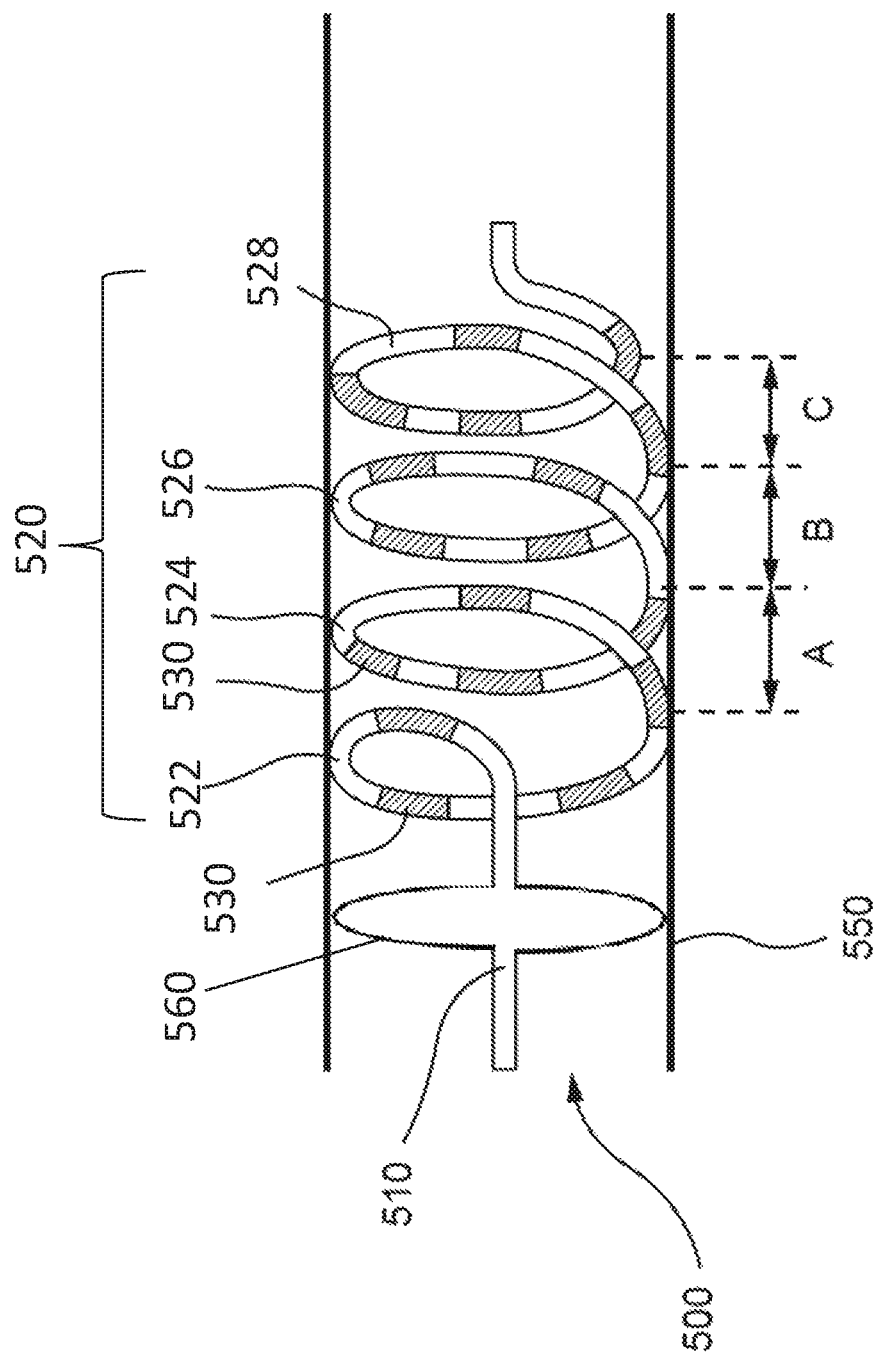
FIG. 5B is a side view of an ablation device disposed in an esophagus according to embodiments.

FIG. 5A is a side view of an embodiment of an ablation device (500) including a first catheter (510) (e.g., outer catheter shaft) coupled to a set of helical loops (520) at a distal end of the catheter (510) extending along a length of the first catheter (510). The first catheter (510) may define a lumen therethrough. The set of helical loops (520) may be configured to maintain a predetermined shape (e.g., diameter, length, winding pitch, etc.) in the absence of a constraint. In some embodiments, as best shown in FIG. 5B, at a given position along a length of the ablation device (500), a set of balloons (560) may be disposed radially about the first catheter (510) of the ablation device (500). FIGS. 5A-5B illustrate a length A between a first loop (512) and a second loop (514), a length B between the second loop (514) and a third loop (516), a length C between the third loop (516) and a fourth loop (518). In some embodiments, a length of the set of loops (520) may be between about 35 mm and about 50 mm. In some embodiments, the lengths A, B, C, may be substantially equal or may vary. For example, a winding pitch may differ between at least two loops of the set of loops (520). In some embodiments, a winding pitch of the set of loops (520) may be substantially equal. For example, each loop of the set of loops (520) may have a winding pitch of about 10 mm. In some embodiments, a winding pitch of the set of loops may be between about 2 mm and about 16 mm. In one embodiment, a winding pitch of the set of loops (520) may increase in a distal direction. For example, a first loop (512) may have a winding pitch between about 2 mm and about 7 mm, and a fourth loop (518) may have a winding pitch between about 6 mm and about 16 mm. The second loop (514) and the third loop (516) may have respective winding pitches between those of the first loop (512) and the fourth loop (518).

A distal end of the device (500) may include an atraumatic shape to reduce trauma to tissue. Each loop of the set of loops (520) may include a set of independently addressable electrodes (530) formed on a surface of the loop (520). Each electrode (530) may include an insulated electrical lead configured to sustain a voltage potential of at least about 700 V without dielectric breakdown of its corresponding insulation. Each loop (520) may include the insulated electrical leads of each electrode (530) formed in a body of the first catheter (510) (e.g., within a lumen of the first catheter (510)). FIGS. 5A-B illustrate a set of loops (520) where each loop includes a set of electrodes (530) having about the same size, shape, and spacing as the electrodes of an adjacent loop. In other embodiments, the size, shape, and spacing of the electrodes (530) may differ.

The ablation device (500) may be configured for delivering a set of voltage pulse waveforms using a set of electrodes (530) to ablate tissue in one or more regions of the esophagus (550). In some of these embodiments, the ablation device (500) may be advanced into an esophagus (550) such that the loops (520) of the ablation device (500) expand outward to allow the electrodes (530) to contact esophageal tissue such as at an inferior portion of the esophagus (550) (e.g., towards a distal end of the device (500)).

In some embodiments, at least a portion of the set of loops (520) may be biased to form an expanded configuration. For example, the ablation device (500) and corresponding set of loops (520) may be slidably disposed within a lumen of an outer sheath (not shown) so as to form a first (e.g., compact) configuration. When the set of loops (520) are advanced out of a distal end of the outer sheath, the set of loops (520) may naturally bias (e.g., deploy) towards the expanded configuration such as shown in FIGS. 5A-5B. In some embodiments, each loop of the set of loops (520) may form a shape with an effective cross-sectional diameter at its largest portion of between about 10 mm and about 25 mm.

In other embodiments, the set of loops (520) may have an asymmetric shape along the length of the ablation device (500), so that one end (say the distal end) of the set of loops (520) has a greater diameter than the other end (say the proximal end) of the set of loops (520). The set of loops (520) may be advanced through the esophagus (150) within a sheath and/or endoscope (not shown) and advanced out of the sheath and/or endoscope to be disposed in contact with esophageal tissue prior to delivering a pulse waveform. In some embodiments, the ablation device (500) may be configured to be slidably disposed within a lumen of an endoscope and/or sheath. In some embodiments, a sheath may be coupled to the endoscope.

In one embodiment, each of the electrodes (530) on a loop may be configured as an anode while each of the electrodes on a different loop may be configured as a cathode. That is, the set of electrodes on adjacent loops may have opposite polarities. In this manner, a cylindrical contiguous ablation lesion may be generated using a set of pulse waveforms applied to the set of electrodes (530). In another embodiment, the electrodes (530) on one loop may alternate between an anode and cathode with the electrodes of another loop having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

In some embodiments, the electrodes may be electrically activated in a sequential manner to deliver a pulse waveform with each anode-cathode pairing. In some embodiments, the electrodes (530) may be electrically wired together within the loop (520), while in alternate embodiments they may be wired together in the handle of the device (500), so that these electrodes (530) are at the same electric potential during ablation. In other embodiments, the size, shape, and spacing of the electrodes (530) may differ as well. As another example, the loops (520) may be activated sequentially in a clockwise or counter-clockwise manner. As another example, the cathode loops may be activated sequentially along with respective sequential anode loop activation until ablation is completed. In embodiments where electrodes (530) on a given loop (520) are wired separately, the order of activation within the electrode (530) of each loop (520) may be varied as well. For example, the electrodes (130) in a loop may be activated all at once or in a predetermined sequence In some embodiments, the catheter shaft may have an inner lumen and in the region of the electrodes, the inner lumen may connect to the outer shaft via one or more openings to deliver irrigation or saline fluid during pulsed electric field ablation.

In some embodiments, the electrodes may be independently addressable, and the electrodes may be energized in any sequence using any pulse waveform sufficient to ablate tissue by irreversible electroporation. It should be appreciated that the size, shape, and spacing of the electrodes on and between the loop may be configured to deliver pulsed electric field energy to ablate one or more regions of the esophagus. In some embodiments, alternate electrodes (for example, all the distal electrodes) can be at the same electric potential, and likewise for all the other electrodes (for example, all the proximal electrodes). Thus, ablation may be delivered rapidly with all electrodes activated at the same time. A variety of such electrode pairing options exist and may be implemented based on the convenience thereof.

Each of the loops (520) may include a polymer and define a lumen so as to form a hollow tube. The set of loops (520) of the ablation device (500) may have a diameter between about 1.0 mm to about 5.0 mm. The set of electrodes (530) of the ablation device (500) may have a diameter between about 1.0 mm to about 5.0 mm and a length between about 0.2 mm to about 5.0 mm.

The ablation device (500) may include any number of loops, for example, 2, 3, 4, 5, 6, 7, 8, 9, 10, 12, 14, 16, 18, 20, or more loops, including all values and sub-ranges in between. In some embodiments, the ablation device (500) may include 3 to 10 loops. For example, the ablation device (500) may include from 3 to 6 loops.

Each of the loops of the set of loops (520) may include respective electrodes (530) having an atraumatic shape to reduce trauma to tissue. For example, the electrodes (530) may have an atraumatic shape including a rounded, flat, curved, and/or blunted portion configured to contact esophageal tissue. In some embodiments, the electrodes (530) may be located along any portion of the loop (520). The electrodes (530) may have the same or different sizes, shapes, and/or location along respective loops. In some embodiments, each loop of the set of loops (520) may include four electrodes (530).

Figure 6A:
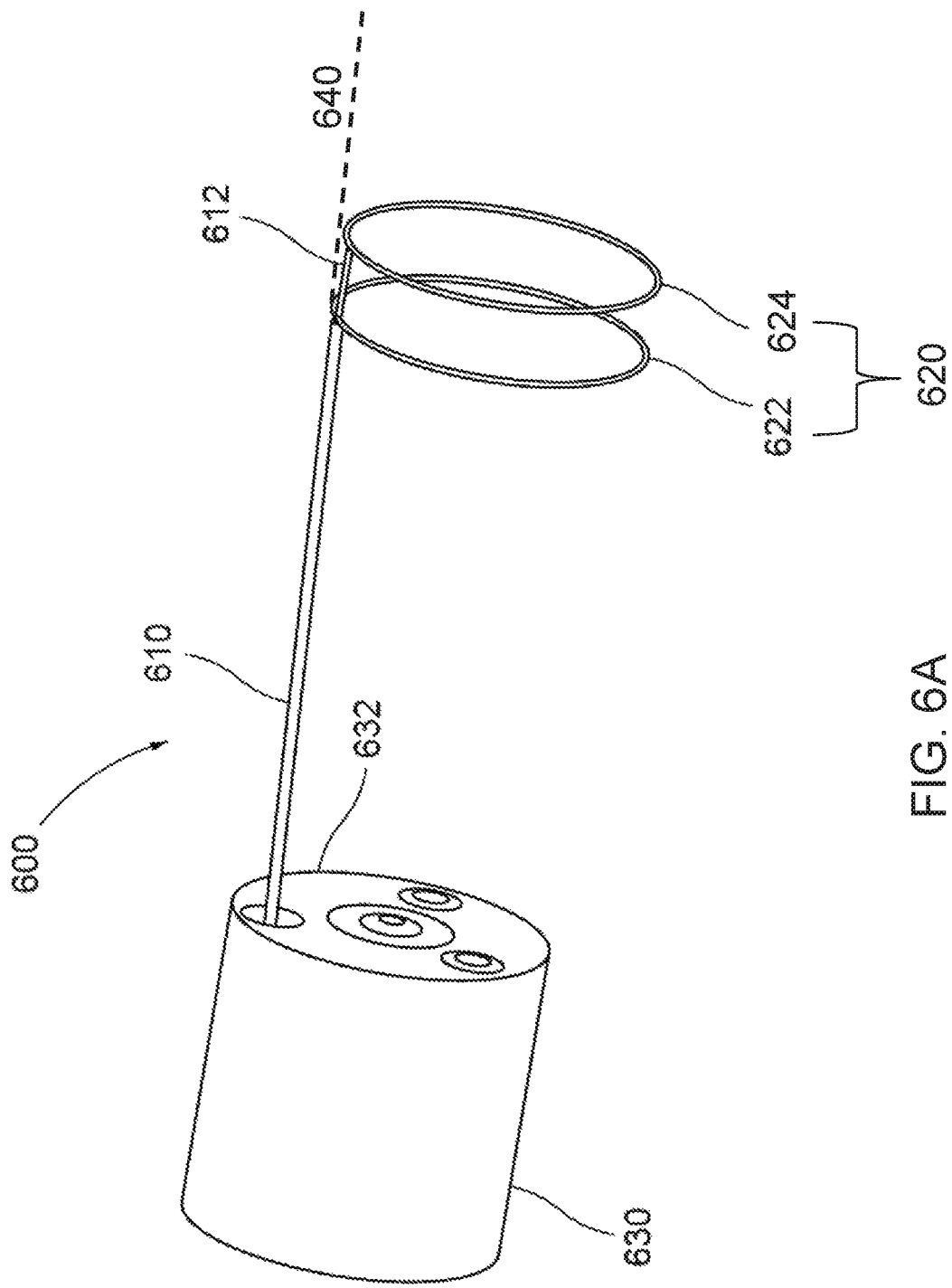
FIG. 6A is a perspective view of an endoscope and ablation device, according to embodiments.
Figure 6B:
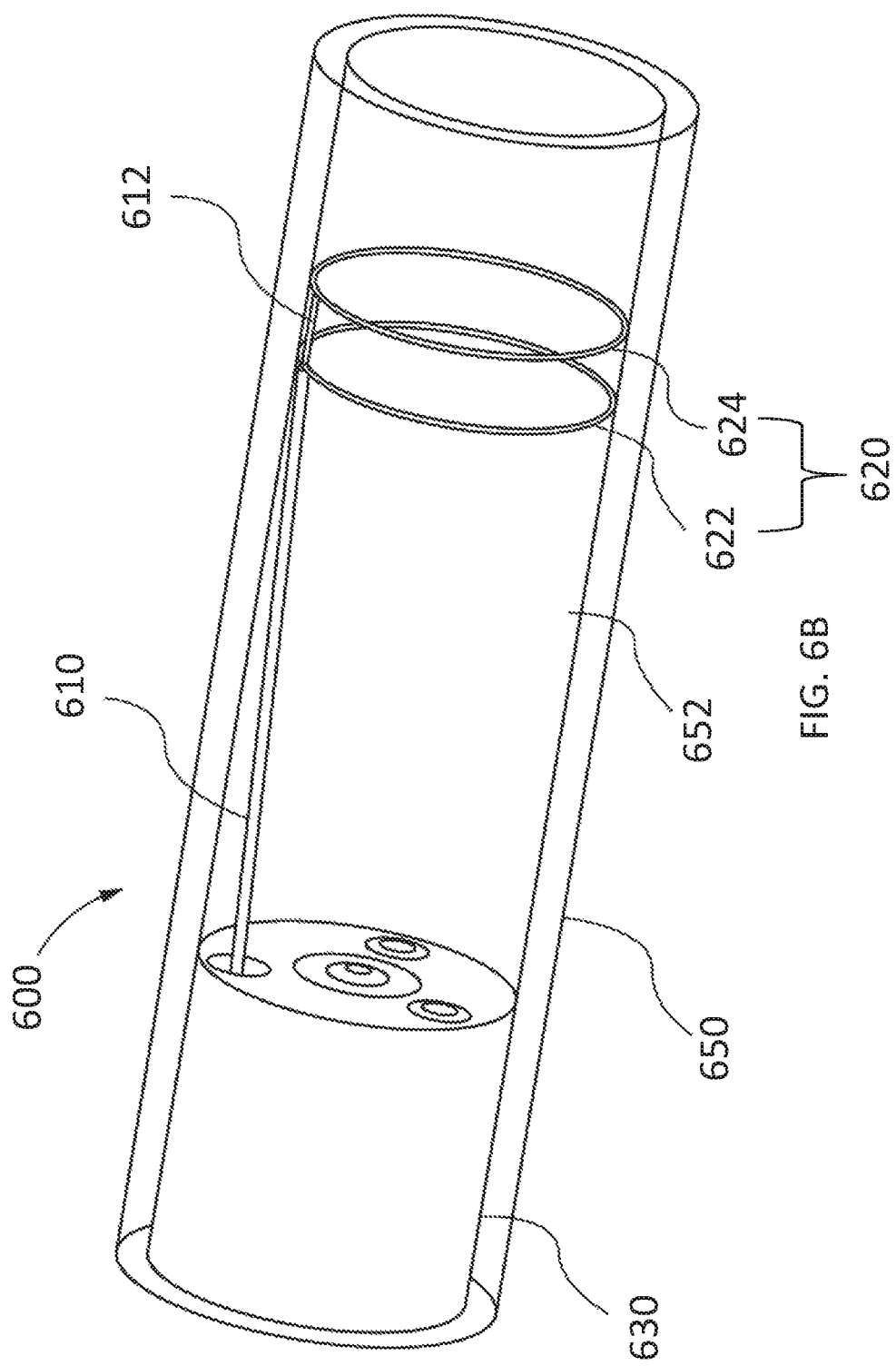
FIG. 6B is a perspective view of an endoscope and ablation device disposed in an esophagus, according to other embodiments.

FIG. 6A is a perspective view of an endoscope (630) and ablation device (600). FIG. 6B is a perspective view of the endoscope (630) and ablation device (600) disposed in an esophagus (650). The ablation device (600) may include a first catheter (610) coupled to a set of independently addressable loop electrodes (620) at a distal end of the catheter (610). The loop electrodes (620) may extend laterally from the catheter (610) since the catheter (610) is in a lumen (632) of an endoscope (630) that is offset from a central longitudinal axis of the endoscope (630). The loop electrodes (620) may be spaced apart from each other along an adjustable length of the first catheter (610) by a first distance. The first catheter (610) may define a lumen therethrough. The set of loop electrodes (620) may be configured to maintain a predetermined shape (e.g., diameter, length, curvature, etc.) in the absence of a constraint. In some embodiments, the set of electrodes may be arranged substantially perpendicular to a longitudinal axis (640) of the first catheter (610) such that the loop electrodes (622, 624) are substantially parallel to each other.

In some embodiments, the first catheter (610) may define a lumen having a second catheter (612) slidably disposed therethrough. A distal end of the first catheter (610) may be coupled to the first electrode (622) and a distal end of the second catheter (612) may be coupled to a second electrode (624). The second catheter (612) may be advanced relative to the first catheter (610) to vary a distance between the first electrode (622) and the second electrode (624).

A distal end of the device (600) may include an atraumatic shape to reduce trauma to tissue. Each electrode (620) may include an insulated electrical lead configured to sustain a voltage potential of at least about 700 V without dielectric breakdown of its corresponding insulation. The first catheter (610) may include the insulated electrical leads of each electrode (620) formed in a body of the first catheter (610) (e.g., within a lumen of the first catheter (610)). FIGS. 6A-6B illustrates a set of electrodes (620) having about the same size and shape as each other. In other embodiments, the size, shape, and spacing of the electrodes (620) may differ.

The ablation device (600) may be configured for delivering a set of voltage pulse waveforms using a set of electrodes (620) to ablate tissue and electrically isolate one or more regions of the esophagus (650). In some of these embodiments, the ablation device (600) may be advanced into an esophagus (650) such that the electrodes (620) contact esophageal tissue (652) such as at an inferior portion of the esophagus (650) (e.g., towards a distal end of the device (600)).

In some embodiments, the ablation device (600) may be slidably advanced from a lumen (632) of an endoscope (630). The lumen (632) may be offset from a central axis of the endoscope (630). In some embodiments, each electrode of the set of electrodes (620) may form a shape with an effective cross-sectional diameter at its largest portion of between about 10 mm and about 35 mm. In other embodiments, the set of electrodes (620) may have varying diameters such that a second electrode (624) has a different diameter than a first electrode (622). In an undeployed configuration, the first electrode (622) may be just distal to the endoscope (630) and may contact the endoscope (630). In some embodiments, a sheath (not shown) may be coupled to the endoscope (630). FIGS. 6A-6B illustrate the device (600) in a deployed configuration where the first catheter (610) may be advanced away from the endoscope (630) by a predetermined distance.

In one embodiment, a first electrode (622) may be configured as an anode while a second electrode (624) may be configured as a cathode. That is, adjacent electrodes may have opposite polarities. In this manner, a cylindrical contiguous ablation lesion may be generated using a set of pulse waveforms applied to the set of electrodes (620). By repeatedly ablating and moving the first catheter (610), a cylindrical length or section of esophagus (650) may be ablated. In some embodiments, movement of the ablation device (600) may be controlled by a motor.

In some embodiments, the electrodes may be electrically activated in a sequential manner to deliver a pulse waveform with each anode-cathode pairing. In some embodiments, the electrodes may be independently addressable, and the electrodes may be energized in any sequence using any pulse waveform sufficient to ablate tissue by irreversible electroporation. It should be appreciated that the size, shape, and spacing of the electrodes may be configured to deliver pulsed electric field energy to ablate one or more regions of the esophagus. A variety of such electrode pairing options exist and may be implemented based on the convenience thereof.

Each of the electrodes (620) may define a lumen so as to form a toroidal shape. The set of electrodes (620) of the ablation device (600) may have a diameter between about 1.0 mm to about 4.0 mm. The ablation device (600) may include any number of electrodes, for example, 2, 3, 4, 5, 6, 7, 8, 9, 10, 12, or more electrodes, including all values and sub-ranges in between. In some embodiments, the ablation device (600) may include 2 to 10 electrodes. For example, the ablation device (600) may include from 2 to 6 electrodes.

Each electrode of the set of electrodes (620) may have an atraumatic shape to reduce trauma to tissue. For example, the electrodes (620) may have an atraumatic shape including a rounded, flat, curved, and/or blunted portion configured to contact esophageal tissue. In some embodiments, the electrodes (620) may be located along any portion of the first catheter (610).

The electrodes as described may be composed of any suitable biocompatible conductive material including, but not limited to, one or more of silver, palladium, stainless steel, platinum, titanium, platinum-iridum alloys, gold, copper, nickel, combinations thereof, and the like. In some embodiments, the electrode materials may be plated, coated, and/or otherwise applied in an appropriately thick layer on top of a different substrate material. In some embodiments, electrode portions may be coupled using annealing, soldering, welding, crimping, lamination, combinations thereof, and the like. The spline, loop, and body of the ablation devices disclosed may be composed of any suitable biocompatible material including metals, glasses, ceramics, polymers, combinations thereof, and the like. The catheter shaft may be made of a flexible polymeric material such as Teflon, Nylon, Pebax, combinations thereof, and the like.

In all the embodiments described in the foregoing and without limitation, the ablation catheter itself may be a steerable device with pull wires for controlling deflection through a suitable mechanism in the catheter handle, as is known to those skilled in the art.

II. Methods

Also described here are methods for ablating tissue (e.g., esophageal tissue) using the systems and devices described above. The ablation devices described herein may be used for ablation of features/structures associated with Barrett's esophagus. Generally, the methods described here include introducing and disposing a device in contact with one or more regions of the esophagus. A set of splines of the device may be deployed and/or one or more balloons of the device may be inflated. Optionally, a conducting fluid may be output from the device. A pulse waveform may be delivered by one or more electrodes of the device to ablate tissue. In some embodiments, the pulse waveforms may include a set of levels of a hierarchy to reduce total energy delivery. This process may be repeated for set of tissue regions to be ablated. It should be appreciated that any of the ablation devices described herein may be used to ablate tissue using the methods discussed below as appropriate.

Figure 9:
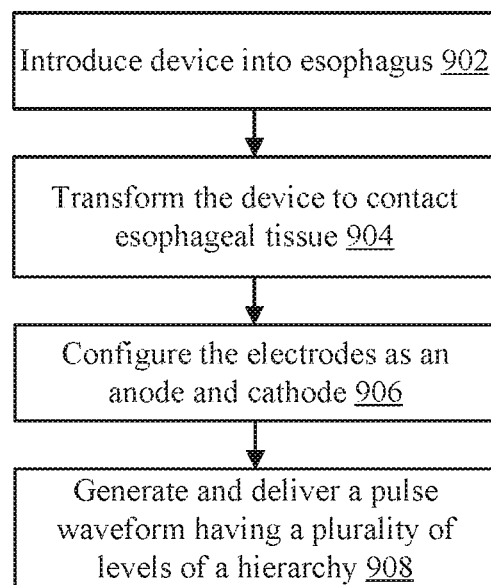
FIG. 9 illustrates a method for tissue ablation, according to embodiments.

As a non-limiting example, in some embodiments, a system can include one or more ablation catheters (e.g., an ablation device as illustrated and described with respect to FIGS. 1-7) useful for ablating tissue. FIG. 9 is a method (900) for one embodiment of a tissue ablation process. Generally, the method (900) includes introduction of a device (e.g., ablation device, such as the ablation device (100), and/or any of the ablation devices (100, 200, 300, 400, 500, 600, 740) into an esophagus of a patient by any suitable means at step (902). For example, the ablation device may be advanced in a lumen of an endoscope and/or outer sheath. In some embodiments, the ablation device may be positioned at an inferior portion of the esophagus.

For any of the steps described herein, an endoscope or other visualization device may be used to visualize tissue (e.g., esophagus) and/or the ablation device to aid and/or confirm the steps being performed. For example, an endoscope may be used to identify one or more portions of the esophagus to ablate and to aid positioning of the ablation device relative to the esophagus. The endoscope may further be used to visualize a configuration of one or more of the balloons and set of splines (e.g., inflated, deflated, basket shape, etc.). The endoscope may be advanced or retracted within the esophagus as needed.

At step 904, the ablation device may be transformed to be in close proximity to and/or in contact with esophageal tissue. For example, a set of balloons may transition from a deflated configuration to an inflated configuration by using an actuation mechanism coupled to a handle of the ablation device. In some embodiments, the set of balloons may be inflated using a fluid such as saline. The inflated configuration may expand the set of balloons such that the balloons may contact and/or apply a force to the walls of the esophagus in order to hold the ablation device in place and to seal off a portion of the esophagus between the balloons from the rest of the esophageal space, following which saline may be infused into the sealed-off portion of the esophagus to provide an electrically conducting environment to aid delivery of pulsed electric field ablation. Furthermore, the set of splines may transition from a first configuration to a second configuration by using another actuation mechanism coupled to a handle of the ablation device. For example, a second catheter coupled to a distal end of the set of splines may be retracted relative to a first catheter coupled to a proximal end of the set of splines to transition the set of splines from the first configuration to the second configuration. The set of splines may be expanded such that they form a basket shape that may bring one or more portions (e.g., intermediate portion) of the set of splines in close proximity and/or in contact with esophageal tissue.

In some embodiments, a conducting fluid (e.g., saline) may be infused into a body cavity (e.g., lumen of esophagus). For example, saline may be injected out of a set of fluid openings in the ablation device increase a conduction volume encompassing the set of electrodes. Saline may be directed towards one or more of the set of splines or towards the space between the splines. Infusing the ablation device and the esophagus with saline may aid electrical conduction between the set of electrodes and esophageal tissue even when one or more electrodes are not in direct contact with tissue.

At step 906, the set of electrodes may be configured in a set of anode-cathode pairings. In some embodiments, the set of electrodes on adjacent splines may have opposite polarities. In another embodiment, the electrodes on one spline may alternate between an anode and cathode with the electrodes of another spline having a reverse configuration (e.g., cathode and anode). In some embodiments, adjacent distal electrodes and proximal electrodes may form an anode-cathode pair. For example, the distal electrodes may be configured as an anode and the proximal electrodes may be configured as a cathode.

At step 908, the electrodes may be electrically activated in a sequential manner to deliver a pulse waveform with each anode-cathode pairing. For example, the set of splines may be activated sequentially in a clockwise or counter-clockwise manner. As another example, the cathode splines may be activated sequentially along with respective sequential anode spline activation until ablation is completed. The electrodes in a spline may be activated all at once or in a predetermined sequence.

In some embodiments, the electrodes may be independently addressable, and the electrodes may be energized in any sequence using any pulse waveform sufficient to ablate tissue by irreversible electroporation. In some embodiments, ablation may be delivered rapidly with all electrodes activated at the same time. A variety of such electrode pairing options exist and may be implemented based on the convenience thereof. In some embodiments, hierarchical voltage pulse waveforms having a nested structure and a hierarchy of time intervals as described herein may be useful for irreversible electroporation, providing control and selectivity in different tissue types. A pulse waveform may be generated by a signal generator (e.g., the signal generator (810)) and may include a set of levels in a hierarchy. A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). The generated pulse waveform may be delivered to tissue. Accordingly, in some embodiments, a contiguous, transmural zone of ablated tissue may electrically isolate the pulmonary vein from a main body of the left atrium.

In some embodiments, the pulse waveform may be delivered to esophageal tissue of a patient via one or more electrodes of an ablation device. In other embodiments, voltage pulse waveforms as described herein may be selectively delivered to electrode subsets such as paired anode-cathode subsets for ablation and isolation of the esophagus. For example, a first electrode of a first spline may be configured as an anode and a second electrode of a second spline may be configured as a cathode.

At step 910, the ablation device may be repositioned to treat other tissue regions. In some embodiments, saline infused into the esophagus may be removed and/or otherwise suctioned out to the extent possible. For example, the ablation device may suction saline using the same fluid openings by which the saline was infused into the esophagus. The set of splines may transition from the second configuration (e.g., basket) to the first configuration. For example, the second catheter may be advanced relative to the first catheter to transition the set of splines from the second configuration to the first configuration. Furthermore, a set of balloons may transition from the inflated configuration to the deflated configuration. In some embodiments, the set of balloons may be deflated by removing fluid from within the set of balloons. The deflated configuration may allow the ablation device to be repositioned within a body cavity such as the esophagus. The ablation device may be moved to another desired location such as another region of the esophagus for tissue ablation. Steps 904-910 may be repeated for a desired number of tissue regions to be ablated.

Pulse Waveform

Disclosed herein are methods, systems and apparatuses for the selective and rapid application of pulsed electric fields/waveforms to effect tissue ablation with irreversible electroporation. The pulse waveform(s) as disclosed herein are usable with any of the systems (800), devices (e.g., 100, 200, 300, 400, 500, 600, 700, 840), and methods (e.g., 900) described herein. Some embodiments are directed to pulsed high voltage waveforms together with a sequenced delivery scheme for delivering energy to tissue via sets of electrodes. In some embodiments, peak electric field values can be reduced and/or minimized while at the same time sufficiently large electric field magnitudes can be maintained in regions where tissue ablation is desired. This also reduces the likelihood of excessive tissue damage or the generation of electrical arcing, and locally high temperature increases. In some embodiments, a system useful for irreversible electroporation includes a signal generator and a processor capable of being configured to apply pulsed voltage waveforms to a selected plurality or a subset of electrodes of an ablation device. In some embodiments, the processor is configured to control inputs whereby selected pairs of anode-cathode subsets of electrodes can be sequentially triggered based on a pre-determined sequence.

In some embodiments, the pulsed voltage waveforms disclosed herein are hierarchical in organization and have a nested structure. In some embodiments, the pulsed waveform includes hierarchical groupings of pulses with a variety of associated timescales. Furthermore, the associated timescales and pulse widths, and the numbers of pulses and hierarchical groupings, can be selected so as to satisfy one or more of a set of Diophantine inequalities.

Pulsed waveforms for electroporation energy delivery as disclosed herein may enhance the safety, efficiency and effectiveness of the energy delivery by reducing the electric field threshold associated with irreversible electroporation, yielding more effective ablative lesions with reduced total energy delivered. This in turn can broaden the areas of clinical application of electroporation including therapeutic treatment of Barrett's esophagus.

Figure 10:
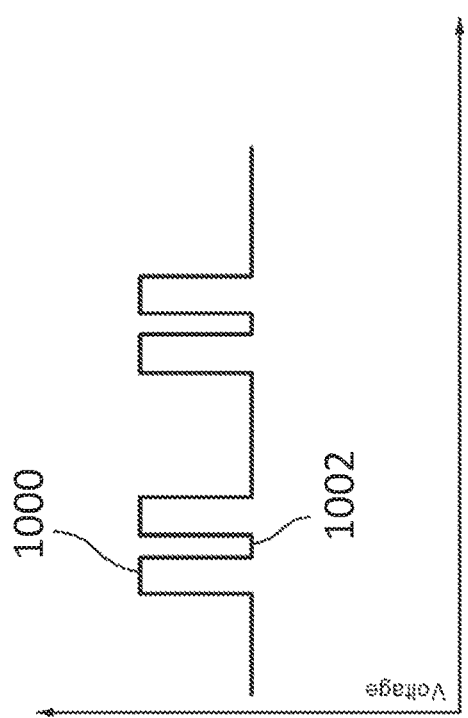
FIG. 10 is an example waveform showing a sequence of voltage pulses with a pulse width defined for each pulse, according to embodiments.

FIG. 10 illustrates a pulsed voltage waveform in the form of a sequence of rectangular double pulses, with each pulse, such as the pulse (1000) being associated with a pulse width or duration. The pulse width/duration can be about 0.5 microseconds, about 1 microsecond, about 5 microseconds, about 10 microseconds, about 25 microseconds, about 50 microseconds, about 100 microseconds, about 125 microseconds, about 140 microseconds, about 150 microseconds, including all values and sub-ranges in between. The pulsed waveform of FIG. 10 illustrates a set of monophasic pulses where the polarities of all the pulses are the same (all positive in FIG. 10, as measured from a zero baseline). In some embodiments, such as for irreversible electroporation applications, the height of each pulse (1000) or the voltage amplitude of the pulse (1000) can be in the range from about 400 volts, about 1,000 volts, about 5,000 volts, about 10,000 volts, about 15,000 volts, including all values and sub ranges in between. As illustrated in FIG. 10, the pulse (1000) is separated from a neighboring pulse by a time interval (1002), also sometimes referred to as a first time interval. The first time interval can be about 10 microseconds, about 50 microseconds, about 100 microseconds, about 200 microseconds, about 500 microseconds, about 800 microseconds, about 1 millisecond including all values and sub ranges in between, in order to generate irreversible electroporation.

Figure 11:
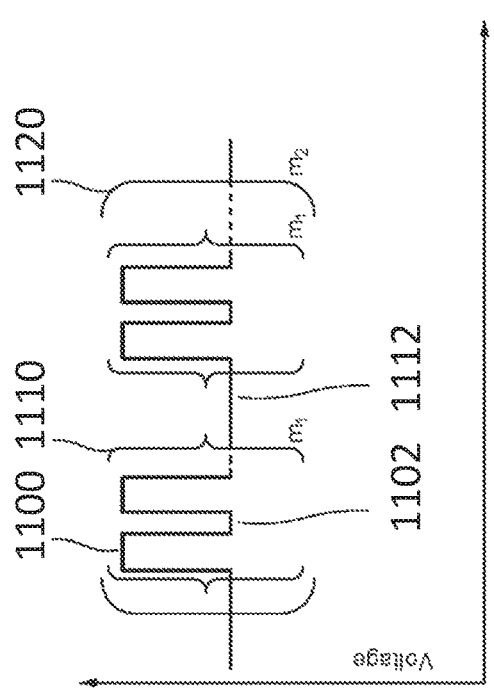
FIG. 11 schematically illustrates a hierarchy of pulses showing pulse widths, intervals between pulses, and groupings of pulses, according to embodiments.

FIG. 11 introduces a pulse waveform with the structure of a hierarchy of nested pulses. FIG. 11 shows a series of monophasic pulses such as pulse (1100) with pulse width/pulse time duration w, separated by a time interval (also sometimes referred to as a first time interval) such as (1102) of duration $t_1$ between successive pulses, a number $m_1$ of which are arranged to form a group of pulses (1110) (also sometimes referred to as a first set of pulses). Furthermore, the waveform has a number $m_2$ of such groups of pulses (also sometimes referred to as a second set of pulses) separated by a time interval (1112) (also sometimes referred to as a second time interval) of duration $t_2$ between successive groups. The collection of $m_2$ such pulse groups, marked by (1120) in FIG. 11, constitutes the next level of the hierarchy, which can be referred to as a packet and/or as a third set of pulses. The pulse width and the time interval $t_1$ between pulses can both be in the range of microseconds to hundreds of microseconds, including all values and sub ranges in between. In some embodiments, the time interval $t_2$ can be at least three times larger than the time interval $t_1$. In some embodiments, the ratio $t_2/t_1$ can be in the range between about 3 and about 300, including all values and sub-ranges in between.

Figure 12:
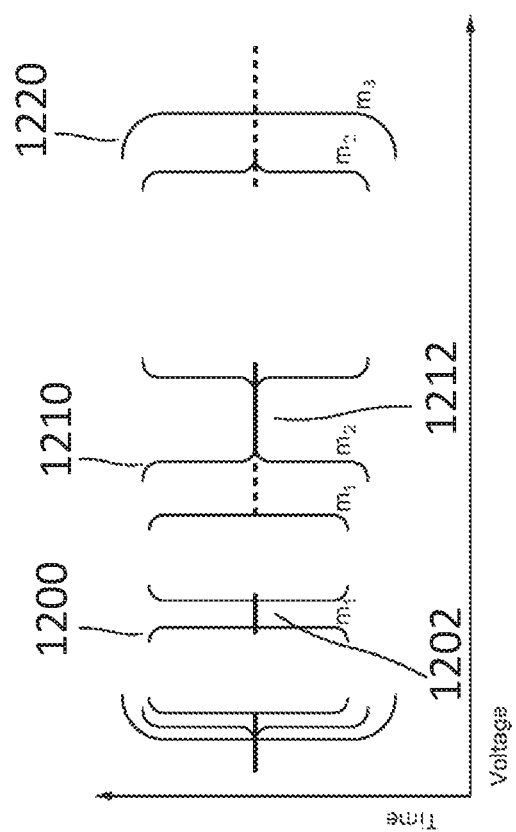
FIG. 12 provides a schematic illustration of a nested hierarchy of monophasic pulses displaying different levels of nested hierarchy, according to embodiments.

FIG. 12 further elaborates the structure of a nested pulse hierarchy waveform. In this figure, a series of $m_1$ pulses (individual pulses not shown) form a group of pulses (1200) (e.g., a first set of pulses). A series of $m_2$ such groups separated by an inter-group time interval (1210) of duration $t_2$ (e.g., a second time interval) between one group and the next form a packet (e.g., a second set of pulses). A series of $m_3$ such packets separated by time intervals (1212) of duration $t_3$ (e.g., a third time interval) between one packet and the next form the next level in the hierarchy, a super-packet labeled (1220) (e.g., a third set of pulses) in the figure. In some embodiments, the time interval $t_3$ can be at least about thirty times larger than the time interval $t_2$. In some embodiments, the time interval $t_3$ can be at least fifty times larger than the time interval $t_2$. In some embodiments, the ratio $t_3/t_2$ can be in the range between about 30 and about 800, including all values and sub-ranges in between. The amplitude of the individual voltage pulses in the pulse hierarchy can be anywhere in the range from 500 volts to 7,000 volts or higher, including all values and sub ranges in between.

Figure 13:
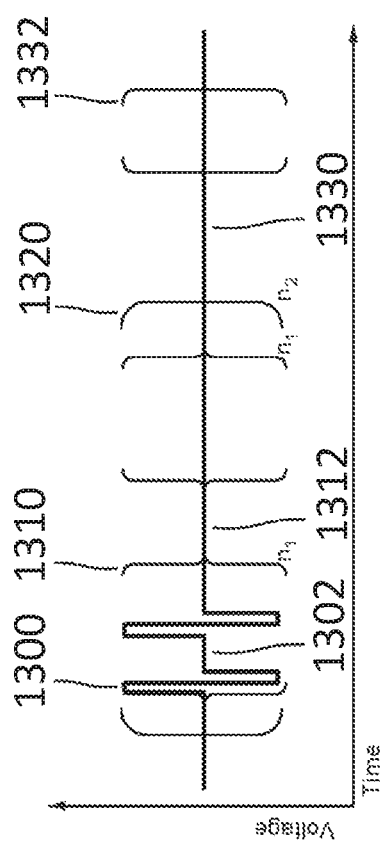
FIG. 13 is a schematic illustration of a nested hierarchy of biphasic pulses displaying different levels of nested hierarchy, according to embodiments.

FIG. 13 provides an example of a biphasic waveform sequence with a hierarchical structure. In the example shown in the figure, biphasic pulses such as (1300) have a positive voltage portion as well as a negative voltage portion to complete one cycle of the pulse. There is a time delay (1302) (e.g., a first time interval) between adjacent cycles of duration $t_1$, and $n_1$ such cycles form a group of pulses (1310) (e.g., a first set of pulses). A series of $n_2$ such groups separated by an inter-group time interval (1312) (e.g., a second time interval) of duration $t_2$ between one group and the next form a packet (1320) (e.g., a second set of pulses). The figure also shows a second packet (1330), with a time delay (1332) (e.g., a third time interval) of duration $t_3$ between the packets. Just as for monophasic pulses, higher levels of the hierarchical structure can be formed as well. The amplitude of each pulse or the voltage amplitude of the biphasic pulse can be anywhere in the range from 500 volts to 7,000 volts or higher, including all values and sub ranges in between. The pulse width/pulse time duration can be in the range from nanoseconds or even sub-nanoseconds to tens of microseconds, while the delays $t_1$ can be in the range from zero to several microseconds. The inter-group time interval $t_2$ can be at least ten times larger than the pulse width. In some embodiments, the time interval $t_3$ can be at least about twenty times larger than the time interval $t_2$. In some embodiments, the time interval $t_3$ can be at least fifty times larger than the time interval $t_2$.

Embodiments disclosed herein include waveforms structured as hierarchical waveforms that include waveform elements/pulses at various levels of the hierarchy. The individual pulses such as (1100) in FIG. 11 includes the first level of the hierarchy, and have an associated pulse time duration and a first time interval between successive pulses. A set of pulses, or elements of the first level structure, form a second level of the hierarchy such as the group of pulses/second set of pulses (1110) in FIG. 11. Among other parameters, associated with the waveform are parameters such as a total time duration of the second set of pulses (not shown), a total number of first level elements/first set of pulses, and second time intervals between successive first level elements that describe the second level structure/second set of pulses. In some embodiments, the total time duration of the second set of pulses can be between about 20 microseconds and about 10 milliseconds, including all values and subranges in between. A set of groups, second set of pulses, or elements of the second level structure, form a third level of the hierarchy such as the packet of groups/third set of pulses (1120) in FIG. 11. Among other parameters, there is a total time duration of the third set of pulses (not shown), a total number of second level elements/second set of pulses, and third time intervals between successive second level elements that describe the third level structure/third set of pulses. In some embodiments, the total time duration of the third set of pulses can be between about 60 microseconds and about 200 milliseconds, including all values and sub ranges in between. The generally iterative or nested structure of the waveforms can continue to a higher plurality of levels, such as ten levels of structure, or more.

In some embodiments, hierarchical waveforms with a nested structure and hierarchy of time intervals as described herein are useful for irreversible electroporation ablation energy delivery, providing a good degree of control and selectivity for applications in different tissue types. A variety of hierarchical waveforms can be generated with a suitable pulse generator. It is understood that while the examples herein identify separate monophasic and biphasic waveforms for clarity, it should be noted that combination waveforms, where some portions of the waveform hierarchy are monophasic while other portions are biphasic, can also be generated/implemented.

It should be understood that the examples and illustrations in this disclosure serve exemplary purposes and departures and variations such as the shape and size of the jaws and electrodes, number of electrodes, and so on can be built and deployed according to the teachings herein without departing from the scope of this invention.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention, which is limited only by the attached claims.

We claim:

1. An apparatus, comprising:
   a first catheter defining a longitudinal axis and a lumen therethrough;
   a balloon coupled to the first catheter, the balloon configured to transition between a deflated configuration and an inflated configuration;
   a second catheter extending from a distal end of the first catheter lumen, the second catheter including a distal cap; and
   a set of splines having a proximal portion coupled to a distal end of the first catheter lumen and a distal portion coupled to the distal cap, each spline including an intermediate portion between the proximal portion and the distal portion, the intermediate portion including a set of electrodes formed on a surface of each of the splines, each electrode having an insulated electrical lead associated herewith, the insulated electrical leads disposed in a body of each of the set of splines, the second catheter configured for translation along the longitudinal axis to transition between a first configuration and a second configuration, wherein:

in the second configuration, each intermediate portion of the set of splines is biased farther away from the longitudinal axis relative to the respective intermediate portion in the first configuration.

2. The apparatus as in claim 1, wherein the set of splines bow radially outward from the longitudinal axis in the second configuration.

3. The apparatus as in claim 1, wherein the set of splines bias away from the longitudinal axis in the second configuration.

4. The apparatus as in claim 1, further comprising an actuator coupled to the set of splines and the distal cap, wherein the actuator is configured to transition the set of splines between the first configuration and the second configuration and the balloon between a deflated configuration and an inflated configuration.

5. The apparatus as in claim 1, wherein the second catheter defines a set of fluid openings.

6. The apparatus of claim 5, wherein the set of openings are oriented towards at least one spline of the set of splines.

7. The apparatus as in claim 1, wherein the balloon is a first balloon and the apparatus includes a second balloon, the second balloon coupled to the second catheter, the second balloon configured to transition between a deflated configuration and an inflated configuration.

8. The apparatus of claim 7, wherein the second balloon is coupled to a distal end of the second catheter.

9. The apparatus as in claim 1, wherein the set of electrodes on adjacent splines have opposite electrical polarities during delivery of voltage pulses.

10. The apparatus as in claim 1, wherein the set of splines when deployed in the second configuration forms a shape with an effective cross-sectional diameter at its largest portion of between about 10 mm and about 35 mm.

11. The apparatus as in claim 1, wherein the set of splines includes between 3 splines and 14 splines.

12. The apparatus as in claim 1, wherein each spline of the set of splines may have a diameter of between about 1 mm and about 4 mm.

13. The apparatus as in claim 1, wherein each electrode of the set of electrodes may have a diameter of between about 1 mm and about 4 mm.

14. The apparatus as in claim 1, wherein the insulated electrical leads are disposed in a body of the second catheter, the insulated electrical leads configured for sustaining a voltage potential of at least about 700 V without dielectric breakdown of its corresponding insulation.

15. The apparatus as in claim 1, wherein the balloon is coupled to a distal end of the first catheter.

16. An apparatus, comprising:

a first catheter defining a longitudinal axis and a lumen therethrough;

a balloon coupled to a distal end of the first catheter, the balloon configured to transition between a deflated configuration and an inflated configuration;

a second catheter extending from a distal end of the first catheter lumen, the second catheter including a distal cap; and a set of splines having a proximal portion coupled to a distal end of the first catheter lumen and a distal portion coupled to the distal cap, each spline including an intermediate portion between the proximal portion and the distal portion, the intermediate portion including a set of electrodes formed on a surface of each of the splines, each electrode having an insulated electrical lead associated herewith, the insulated electrical leads disposed in a body of each of the set of splines, the second catheter configured to transition between a first configuration and a second configuration, wherein:

in the second configuration, each spline of the set of splines is biased farther away from the longitudinal axis relative to the respective spline in the first configuration.

17. A system, comprising:

a signal generator configured for generating a pulse waveform;

an ablation device coupled to the signal generator and configured for receiving the pulse waveform, the ablation device including:

a handle;

a first catheter defining a longitudinal axis and a lumen therethrough;

a balloon coupled to the first catheter, the balloon configured to transition between a deflated configuration and an inflated configuration;

a second catheter extending from a distal end of the first catheter lumen, the second catheter including a distal cap; and a set of splines having a proximal portion coupled to a distal end of the first catheter lumen and a distal portion coupled to the distal cap, each spline including an intermediate portion between the proximal portion and the distal portion, the intermediate portion including a set of electrodes formed on a surface of each of the splines, each electrode having an insulated electrical lead associated herewith, the insulated electrical leads disposed in a body of each of the set of splines, the second catheter configured for translation along the longitudinal axis to transition the set of splines between a first configuration and a second configuration, wherein:

in the second configuration, each intermediate portion of the set of splines is biased away from the longitudinal axis relative to the respective intermediate portion in the first configuration.

18. The system as in claim 17, the pulse waveform including:

a first level of a hierarchy of the pulse waveform includes a first set of pulses, each pulse having a pulse time duration, a first time interval separating successive pulses;

a second level of the hierarchy of the pulse waveform includes a plurality of first sets of pulses as a second set of pulses, a second time interval separating successive first sets of pulses, the second time interval being at least three times the duration of the first time interval; and a third level of the hierarchy of the pulse waveform includes a plurality of second sets of pulses as a third set of pulses, a third time interval separating successive second sets of pulses, the third time interval being at least thirty times the duration of the second level time interval.

* * * * *